(12) United States Patent
Rapp et al.

(10) Patent No.: US 10,973,413 B2
(45) Date of Patent: Apr. 13, 2021

(54) ADVANCED COMPRESSION GARMENTS AND SYSTEMS

(71) Applicants: Scott Rapp, Mountain View, CA (US); Gary Rapp, Dublin, OH (US)

(72) Inventors: Scott Rapp, Mountain View, CA (US); Gary Rapp, Dublin, OH (US)

(73) Assignee: FIOMET VENTURES, INC., Cincinnati, OH (US)

( * ) Notice: Subject to any disclaimer, the term of this patent is extended or adjusted under 35 U.S.C. 154(b) by 570 days.

(21) Appl. No.: 15/289,071

(22) Filed: Oct. 7, 2016

(65) Prior Publication Data

US 2017/0100300 A1   Apr. 13, 2017

Related U.S. Application Data

(60) Provisional application No. 62/238,522, filed on Oct. 7, 2015.

(51) Int. Cl.
| | |
|---|---|
| *A61B 5/01* | (2006.01) |
| *A41D 1/00* | (2018.01) |
| *A61F 13/06* | (2006.01) |
| *A61F 5/01* | (2006.01) |
| *A61F 5/00* | (2006.01) |
| *A61B 5/00* | (2006.01) |

(52) U.S. Cl.
CPC ............... *A61B 5/01* (2013.01); *A41D 1/002* (2013.01); *A61B 5/0053* (2013.01); *A61B 5/6804* (2013.01); *A61B 5/6824* (2013.01); *A61B 5/6828* (2013.01); *A61F 5/00* (2013.01); *A61F 5/0104* (2013.01); *A61F 13/06* (2013.01)

(58) Field of Classification Search
CPC .. A61H 9/005–0092; A61H 2201/5023; A61H 2201/0543–5046; A61H 2201/0103; G01L 1/20; G01L 1/00; A61F 13/06; A61F 5/0104; A61F 5/00; A41D 1/002; A61B 5/01; A61B 5/6824; A61B 5/6804; A61B 5/0053; A61B 5/6828
USPC ............ 73/763, 818–824, 862.621–862.622; 601/84, 103, 151, 150, DIG. 23
See application file for complete search history.

(56) References Cited

U.S. PATENT DOCUMENTS

| | | | | |
|---|---|---|---|---|
| 5,780,746 | A * | 7/1998 | Brady | G01L 1/2281 73/763 |
| 6,194,692 | B1 * | 2/2001 | Oberle | H05B 3/34 219/528 |
| 7,068,142 | B2 * | 6/2006 | Watanabe | H01C 10/106 338/114 |
| 8,308,489 | B2 * | 11/2012 | Lee | H01R 13/2407 2/69 |
| 8,948,839 | B1 * | 2/2015 | Longinotti-Buitoni | A61B 5/6804 29/825 |
| 9,625,330 | B2 * | 4/2017 | Park | G01L 1/205 |
| 9,766,140 | B2 * | 9/2017 | Hou | G01L 1/16 |
| 9,932,697 | B2 * | 4/2018 | Chung | A61B 5/0408 |

(Continued)

*Primary Examiner* — Tu A Vo
*Assistant Examiner* — Alexander Morales
(74) *Attorney, Agent, or Firm* — Business Patent Law, PLLC; Kenneth F. Pearce

(57) ABSTRACT

Advanced compression garments and their methods of use, including garments with compression applying straps, and associated sensors that are able to sense the compression applied to an underlying body tissue by the straps. Pressure and/or temperature information from the sensors may be conveyed to a wearer of the garment and/or to another party.

32 Claims, 18 Drawing Sheets

(56) References Cited

U.S. PATENT DOCUMENTS

| | | | | |
|---|---|---|---|---|
| 10,369,075 B2* | 8/2019 | Mayer | .................. | A43B 3/0005 |
| 2002/0076948 A1* | 6/2002 | Farrell | ...................... | B32B 3/08 |
| | | | | 438/800 |
| 2003/0211797 A1* | 11/2003 | Hill | ...................... | D03D 1/0088 |
| | | | | 442/205 |
| 2006/0182297 A1* | 8/2006 | Cyr | ........................ | A41D 1/005 |
| | | | | 381/333 |
| 2006/0258205 A1* | 11/2006 | Locher | .................. | H05K 1/038 |
| | | | | 439/517 |
| 2007/0177298 A1* | 8/2007 | Jaatinen | ............. | H01R 13/6205 |
| | | | | 360/123.56 |
| 2007/0202765 A1* | 8/2007 | Krans | .................. | G06F 3/0414 |
| | | | | 442/301 |
| 2008/0195018 A1* | 8/2008 | Larson | ............... | A61B 17/1325 |
| | | | | 602/53 |
| 2008/0282665 A1* | 11/2008 | Speleers | .................. | D02G 3/12 |
| | | | | 57/212 |
| 2009/0058440 A1* | 3/2009 | Miura | ............... | G01R 1/07314 |
| | | | | 324/750.16 |
| 2011/0245732 A1* | 10/2011 | Mravyan | ............... | A61B 5/1116 |
| | | | | 600/587 |
| 2012/0062245 A1* | 3/2012 | Bao | ........................ | H01L 29/84 |
| | | | | 324/661 |
| 2012/0123232 A1* | 5/2012 | Najarian | ............. | A61B 5/0022 |
| | | | | 600/345 |
| 2015/0212541 A1* | 7/2015 | Lu | .......................... | G04G 17/02 |
| | | | | 361/679.03 |
| 2015/0297437 A1* | 10/2015 | Neuenhahn | .......... | A61B 5/4848 |
| | | | | 601/148 |
| 2016/0022528 A1* | 1/2016 | Wyatt | .................... | A61H 7/007 |
| | | | | 601/152 |

* cited by examiner

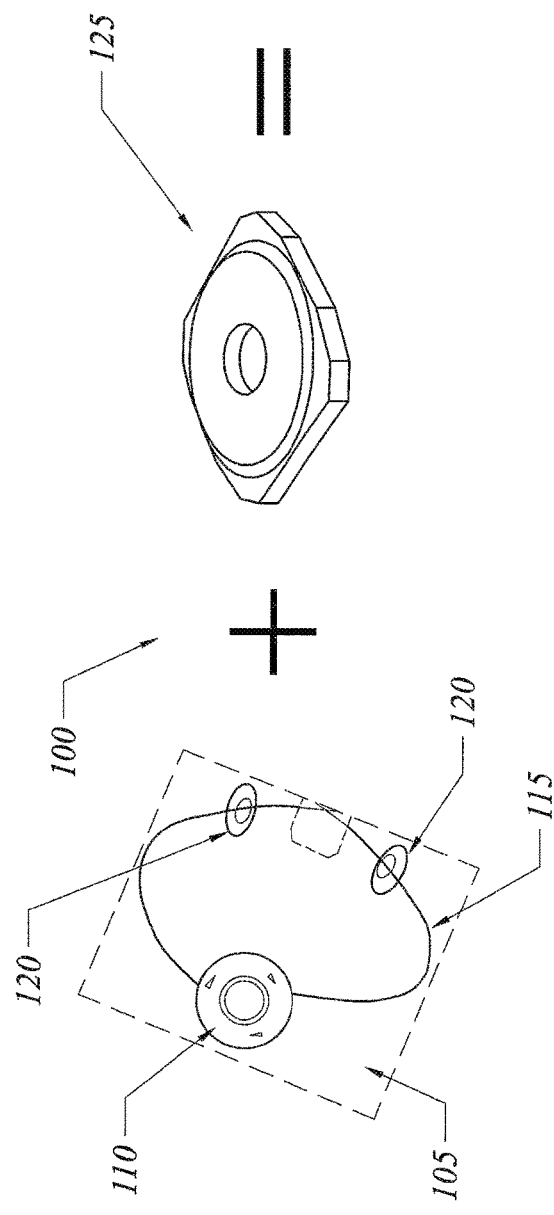
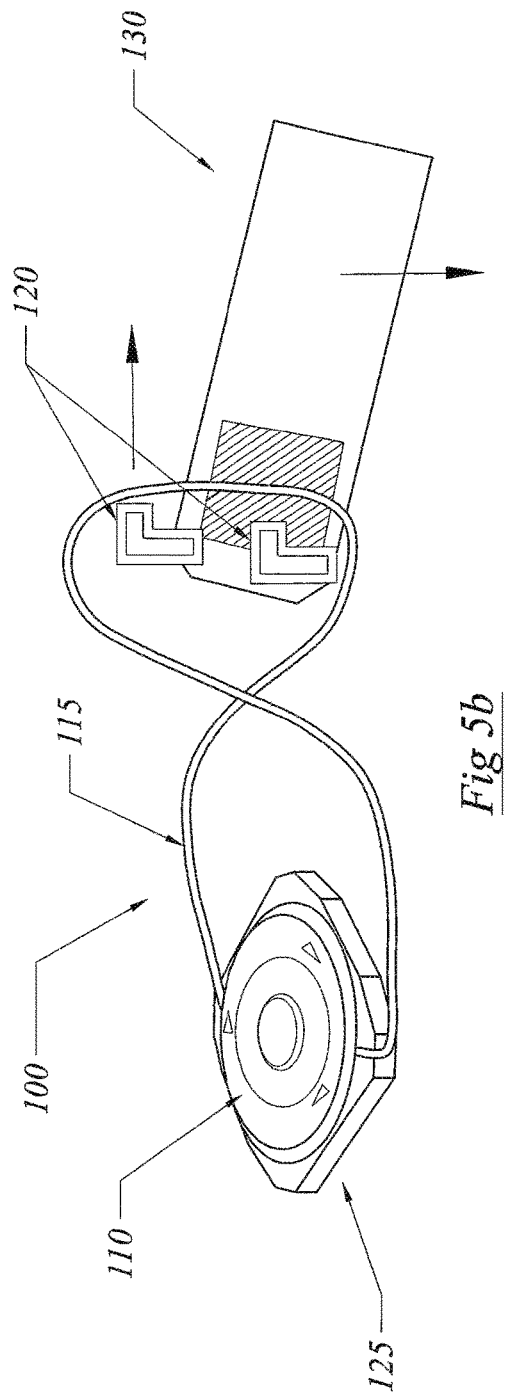
Fig 5a
Fig 5b

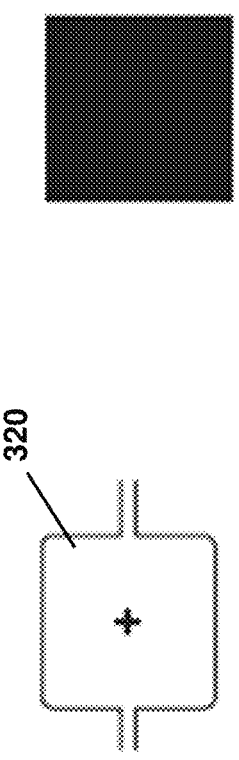
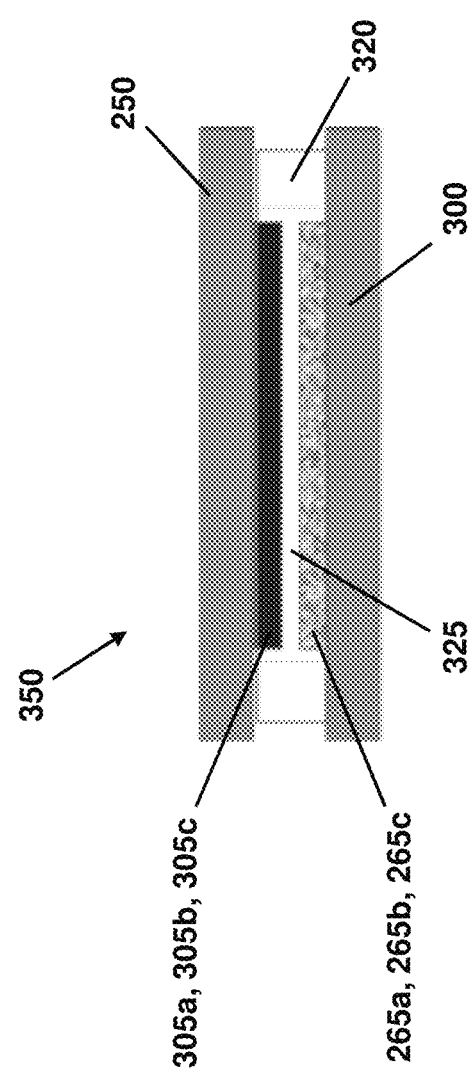
FIG. 9A
FIG. 9B

ADVANCED COMPRESSION GARMENTS AND SYSTEMS

CROSS-REFERENCE TO RELATED APPLICATIONS

This application claims the benefit of U.S. Provisional Application No. 62/238,522, filed on Oct. 7, 2015, which is hereby incorporated by reference as if fully recited herein.

TECHNICAL FIELD

Exemplary device and system embodiments disclosed herein are directed to advanced compression garments.

BACKGROUND

It is known that venous blood pooling or hypertension in humans can lead to health problems including but not limited to muscle/skin injuries, edema, and deep vein thrombosis (DVT). The causes of venous blood pooling may vary, from muscle overuse during aerobic activity, to prolonged immobility such as due to illness or air travel, to reduced blood pressure as a result of general anesthesia. Regardless of the cause, venous blood pooling or hypertension and the related consequences are a concern for all involved.

With respect to venous blood pooling and resultant muscle injuries as a result of aerobic activity, it is notable that running as a source of general exercise continues to grow within the United States. For example, one study indicates a 300% overall increase in the number of runners who have enrolled in competitive races between 1990 and 2013. In 2014 alone, 18,750,000 persons in the U.S. were recorded as having finished running races at distances from 5 k to a full marathon[1]. Females accounted for 57% of those race participants vs. 43% for males, with the median age for all runners being between 25-44 and composing more than half of the total finishing runners. While 18,750,000 runners no doubt indicates a significant interest in running, it does not even include those persons engaged only in recreational running or in casual running as part of an exercise regimen.

Long distance competitive running for health and sport has also seen sharp annual increases in participants. In this regard, RunningUSA.com reports a 77% increase in such runners over the last decade, with more than 2 million participants finishing a half marathon and over 500,000 participants finishing a full marathon across the country.

As an increasing number of people participate in running-based aerobic exercise, there has developed an increasing desire to monitor performance. To this end, wearable sensor technology development and implementation has grown tremendously and the use of such devices on a daily basis is now quite common. For example, it is estimated that 70 million Fitbit activity tracking devices were sold worldwide in 2014. The inventing company of the Fitbit devices quotes figures from IDC estimating that the market for such wearable devices will reach 114.0 million units shipped in 2018, indicating a significant additional increase in aerobic activity participants.

Participation in particular sports requiring long periods of aerobic activity such as running has also grown. For example, soccer is regarded as the most popular sport in the world and has the largest participant population on an amateur level. In fact, it is estimated that there are 200 million amateur soccer players worldwide. Similarly, it is estimated that just in the U.S., there are between 11 and 12 million tennis players, and each year over 1 million high schoolers play football and between 41-52 million cycle. Thus, it is very evident that a large number of individuals engage in activities involving running, whether for general exercise purposes, in running competitions, or during other sports in which a significant amount of running is inherently involved. Participation in sports where other repetitive muscle contraction is involved is also high.

Aerobic exercise involving running provides many health advantages. Resulting physiological changes may include the lowering of harmful cholesterol, a reduction of resting blood pressure, the regulation of blood sugar levels, a reduction in cardiac disease, and improvements in extremity perfusion. Such activity has also been reported to decrease overall depression and stress, elevate mood and boost the immune system. A reduction in the incidence of tension and migraine headaches, as well as a reduction in the incidence of breast cancer, has also been reported[2].

Running may also provide a social environment that facilitates human interaction and connection. The societal, financial, and economic impact of exercise running on global health is substantial.

While running-based aerobic activity may impart numerous benefits, it is known that increases specifically in recreational running have also led to a large numbers of injuries. For example, a study by van Mechelen et al. reports an overall yearly incidence of running injuries to be between 37%-56%[3]. According to this study, roughly 50%-75% of these injuries occur as a result of overuse or repetition, and possibly from improper preparation. Further, failure to recognize the mechanical insult led to a recurrence of injury in 20%-70% of the cases reported, and also to medical treatment. Up to 5% of these injuries result in work days lost. The factors leading to the high rates of muscle, tendon, and joint injury can be, at least in part, attributed to multiple factors including running surface, quality of shoes, orthotics, nutrition, frequency of exercise, and overexertion. The examples of specific overuse injuries associated with running are many. Of these injuries, Iliotibial Band Syndrome (ITBS)/Iliotibial Band Friction Syndrome (ITBFS) is considered to be one of the most common in the lower extremities, affecting anywhere from 7%-14% of the running population[4].

Injuries resulting from running during sports participation are also common. For example, soccer injuries related to muscle trauma are frequent. Published literature reports an incidence of 10-35 injuries per 1,000 soccer practice hours. Myofascial pain resulting from muscle strain, pull, or tightness was reportedly responsible for 45.6% of all of said injuries[5]. The Federation Internationale de Football Association (FIFA) reports an average treatment cost of 150 U.S. dollars for every injury, with an estimation of 30 billion dollars spent worldwide on such injuries[6]. Further, one-third of all injuries in professional soccer are reported to be muscle injuries, with the vast majority of said injuries affecting the hamstring, adductors, quadriceps and calf muscles. One published study from the English Premier League in 2010/2011 reported the average amount lost by each professional team due to player injures associated with muscle physiologic insult to be around 19-26 million dollars, including out-of-pocket expenses in lost wages due to inactivity[7].

The cause of muscle injuries during aerobic exercise and sports participation may be attributed to the physical effort of the participant exceeding the physiologic capability of given muscle and tissue to respond to the correspondingly increased oxygen demand.

What happens during exercise on a muscle cellular level is well documented. Generally speaking, an ischemic environment is created by increased metabolic activity with consumption of oxygen and ATP. The shift towards lactic acid production after depletion of energy stores leads to vasodilation and increased systemic blood flow with shunting from splanchnic blood flow. An autonomic regulatory response to lowering of mean arterial blood pressure is the release of adrenergic factors. A byproduct of the adrenergic and cardiovascular response to increased muscle contraction is thermal output. The effect of these autonomic neural and cardiovascular responses are a focused distribution of cardiac output to the cutaneous circulation aiding heat dissipation and, thus, body temperature regulation (i.e., evaporative or sweat loss). This increase in local and core temperatures leads to an attenuation of α-adrenergic-mediated vasoconstriction resulting from serial skeletal muscle contraction, a phenomenon referred to as functional sympatholysis[8]. This leads to further vessel dilation and increased blood flow to tissues under stress. The increased temperature of skeletal muscle is dependent on exercise intensity.

Heat stress in turn reflexively causes a hyper-adrenergic state associated with increased cardiac output, muscle and skin sympathetic nerve activity, and circulating noradrenaline (norepinephrine) concentrations[9]. There is also heightened extremity and systemic perfusion, and an increase in vascular conductance that occurs during exercise.

The generation of heat may be important in allowing a muscle to "warm up" in anticipation of higher workloads. For example, elevations in leg muscle and skin temperatures to around 37° C. can lead to localized vasodilation to muscle microvasculature, with core temperatures at rest to 38° C.-39° C. also leading to similar increases in perfusion. Thus, both external and systemic heat stress may contribute substantially to exercise limb hyperemia. For example, one study demonstrates that heat stress leads to significant increases in deep, femoral venous oxygen content, quadriceps tissue oxygenation, and leg tissue blood flow, in parallel with significant reciprocal reductions in leg tissue oxygen extraction, in conditions where arterial oxygen content and leg maximal oxygen consumption ($VO_2$) remained essentially unchanged[10].

Moreover, a second study supports the above findings that an increase in leg tissue perfusion during running exercise causes significant reductions in leg arterial-venous oxygen saturation differences. This suggests improved oxygen delivery and extraction to muscles and less shunting towards lactic acid formation (a contributor to muscle cramping and pain)[11].

As skin and muscle generates heat, and induces vessel dilation, the mean arterial blood pressure (MAP) can decrease. The consequential physiologic human response is to increase the heart rate, heart contractibility, and cardiac output. This ability of the heart to change its force of contraction and stroke volume as a result to changes in venous return is known as the Frank-Starling Curve.

As adaptive as the human body may be, the body's ability to harmoniously adapt to physiologic stress can nonetheless be exceeded. With increased metabolic activity and high heat output, the redistribution of blood flow to areas in need can result in orthostatic intolerance. This may manifest clinically as end organ underperfusion, e.g., pre-syncope (dizziness) or syncope (fainting) associated with the brain, low urine output or hematuria associated with the kidneys, or intestinal mucosal sloughing associated with the bowel. Creatinine kinase and serum myoglobin levels also increase with muscle tissue breakdown, possibly leading to kidney dysfunction. Likewise, pro-inflammatory cytokines are released such as IL-6, which can further exacerbate pain, core temperature and muscle damage. Hyperthermia can occur and elevated temperatures deplete glycogen (energy) stores at a more rapid rate. There is reduced baroreflex control with extreme exercise leading to diminished autoregulation of arterial blood pressure despite increases in heart rate and contractility. During exercise, increased capillary hydrostatic pressure caused by elevation of arterial pressure produces plasma volume shifts from the vascular space to the interstitial fluids. Venous pooling occurs with increased sympatholytic activity and diminished vasoconstriction on the microcirculatory level. This may manifest as edema, hypervolemia or venous hypertension.

Age is also an important factor on how the body responds to exercise stress. The published literature shows that increased heart rate and cardiac output ability is inversely proportional with age. Older individuals lack the ability to achieve suitable heart rates in relation to muscle demand level, and stroke volume has been demonstrated to fall progressively with increased exercise. This population is felt to lack an ionotropic (sympathic) response to exercise stress and to instead rely on a chronotropic (cardiac) response that may be insufficient[12].

Dehydration also affects muscle dynamics. Hemoconcentration occurs as intravascular volume decreases after evaporative heat loss. Muscle activation and strength of contraction is lessened[13]. Lower perfusion to the skin prevents further reductions in core body temperature and exacerbating hyperthermia. One study observed sprinters during intense physical demand and demonstrated that elevations in core body temperature decreased overall muscle power output thought to be a result of direct influence on the central nervous system[14]. Autoregulation from hyperthermia may be an alternative negative contributor to muscle performance as seen with other harmful metabolic byproducts (i.e., lactic acid).

In light of the possible negative effects associated with exercise stress, such as the prolonged exercise stress often produced by running, various mitigation devices have been developed. One such device is a compression garment. The use of compression garments, particularly during running, has grown in popularity.

The use of compression during exercise is thought to help with overall circulation and reduce venous pooling. Reducing venous pooling improves venous return, which results in an increase in cardiac preload. While the autonomic response of the body increases heart rate according to the Frank Starling curve, the stroke volume or ability to deliver blood volumes is dependent on cardiac output. Cardiac output, in turn, is dependent on preload dynamics. By increasing cardiac preload, stroke volume may improve (CO×HR).

Some data has also shown improvements in post-exercise recovery and discomfort when compression garments or stockings are used[14]. The use of compression garments during exercise and post-exercise may also help clear interstitial maleficent metabolites. For example, one study demonstrates decreased blood lactate levels following a recovery of 30 minutes when compression garments were worn[15].

There appear to be legitimate benefits to the wearing of compression garments both during and after aerobic exercise. However, determining what level of compression (i.e., pressure) to apply with such compression garments (or other compressive and supportive materials such as tapes) is currently highly anecdotal. Furthermore, it is very difficult to reliably reproduce a given set of compressive pressures for every individual in every running or exercise scenario. This problem is exacerbated by the fact that exercise is a dynamic process with changing body flow and volume states, whereas the compression applied by a given compression garment is static and unchanging. It is moreover very difficult to globally and objectively determine what levels of compression lead to the most ideal response due these fluid changes in cardiovascular efforts. Consequently, there is little reproducible or validated literature providing a uniform consensus on appropriate use with the compression garments currently on the market.

Based on the foregoing disclosure, it should be apparent that there is an ongoing need to prevent or at least reduce the severity and/or frequency of aerobic exercise-related injuries. However, despite education and prevention measures, a uniform and accepted way to prevent muscle injury during athletics and exercise is lacking. While data suggests that the use of compression garments may be beneficial to injury reduction, there is currently no way to determine or ensure that the proper amount of compression will be applied by a given compression garment to a given individual under a particular circumstance. Exemplary device and system embodiments disclosed herein are directed to solving this problem.

SUMMARY

Exemplary device and system embodiments disclosed herein are directed to advanced compression garments that are capable of sensing the functional state of the muscles and overlying skin over which said garments are donned, and to systems in which sensed information may be reported by an advanced garment and provided to a user thereof and/or to another interested party. Exemplary advanced compressions may be used prior to, during and/or after exercise, and also within the medical field, and information sensed by such garments may be utilized to assist in the circulatory optimization of blood flow return. That is, exemplary advanced compression garments and advanced compression garment systems may be used during prolonged exercise to reduce venous blood pooling and venous hypertension by mechanically reducing cardiac afterload in an effort to improve the aforementioned Frank-Starling curve towards idealized cardiovascular physiology. Additionally at rest, functional state data can be gleaned and used for relative evaluation of muscle/skin perfusion in a static physiologic environment.

It is believed that providing additional information regarding muscle perfusion and physiologic state may be beneficial to reducing overall running-associated and other exercise injuries and to reducing secondary sequlae. It is further believed that the use of exemplary garments described herein may allow for optimized exercise performance while simultaneously reducing the incidence of injury. Moreover, in the medical arena, observing real time changes of blood perfusion to muscle and overlying skin may reduce human-related error resulting from applying excessive overlying external pressure from bandages such as casting or splinting material, dressings, compression garments, and padding in the operating theater. Increased pressures observed over time will inversely correlate with decreased tissue perfusion below the sensor. Providing notification of severe pressure changes may in turn reduce overall morbidity of skin ulceration and possible muscle death during acute injury.

One exemplary advanced compression garment embodiment is a compression sleeve that is designed to exert a compressive force on a limb of a user when worn. Such a compression sleeve embodiment may be designed for and worn on an upper arm, forearm, calf or thigh, for example. Exemplary sleeve embodiments may be of layered construction. An inner layer of an exemplary sleeve may act as a comfort layer. For example, the inner layer may protect the underlying tissue against any contour irregularity associated with one or more sensors (see below) associated with the sleeve. This layer may have silicone or an adhesive material applied to its inner surface to prevent rotation or slippage. The inner layer may also be composed of a material that has silicone woven therein to provide greater comfort and uniformity of adhesive materials. Furthermore, the inner layer may be woven with an electro-conductive thread (e.g., silver thread), such that with a small electrical current applied, the garment will heat up. The inner layer may also act to retain the sleeve on the limb of a user at least until outer compressive straps are secured (see below). The inner layer may employ a zipper, small hooks, a hook and loop assembly (e.g., Velcro®) to assist with sleeve retention. The inner layer may also be the surface upon which the sensor is placed. The inner layer may also be used alone to provide data on muscle dynamics without external compression.

A layered exemplary sleeve embodiment may also include an outer layer that overlies the inner layer. The outer layer is preferably adapted to provide graded compression to the underlying limb musculature. For example, the outer layer may be a strap, or may be divided into individual straps of some width, that can be wrapped at least partially around the limb. Preferably, each strap may be adjusted for proper tightness (compression) to provide an increasing pressure gradient along (up) the limb so as to help push blood back to the heart in the venous system as well as the interstitium.

Straps associated with an exemplary advanced compression garment may have silicone or other adhesive materials woven therein to provide greater adherence to the underlying inner garment layer or the skin of a wearer. Additionally, the outer straps may contain synthetic muscle or polymers that can contract upon application of small electrical currents to allow for sequential or serial compression. Such polymers may be composed of monofilaments, carbon nanotubules, or equivalent structures.

Strap tension and, therefore, resulting compression, may be achieved in various ways. For example, securing a strap with Velcro, magnets, adhesives, or the like will provide gross pressure application. If a more accurate and repeatable application of pressure is desired, a more precise method of strap securement, such as a reel and lace closure system or a similar securement technique, may be employed. A motorized reel and lace system is also a possibility, and may be paired to a controller that causes the motor to apply a particular tension to the strap(s). Synthetic muscle may also be used apply a force to the straps resulting from contracture in length following electrical current application. When circumferentially placed around a limb, a greater force and compression will be generated to underlying skin/muscle as the overall diameter of the garment decreases.

As mentioned above, at least one sensor is associated with an exemplary compressive garment embodiment. The at least one sensor may employ, for example, a force-sensing resistor (FSR) or piezoelectric disc sensor technology. The sensor(s) will be placed in close proximity to the skin and, when multiple sensors are present, may be arranged in series or placed in customizable positions according to the location of underlying muscle fibers to be monitored. For example, a sensor may be located to underlie each strap present on a given advanced compression garment. Alternatively, the inner layer of a given advanced compression garment may be comprised of piezoelectric fabric, whereby the entire inner layer will be pressure and temperature sensing along the entirety thereof. Other sensor technologies may also be used, such as measuring resistance changes through woven silver threads as they are deformed.

The sensor(s) of a given advanced compression garment will be capable of observing pressure and temperature associated with the underlying tissue. Since local heat stress causes increases in muscle blood flow, surface temperature can be used to detect and gauge an increase in muscle perfusion. Active surface temperature readings can be used to inform the wearer or another party of the warmth a muscle, which may be used to indicate the readiness of the muscle to engage in more strenuous activity. When an electro-active thread (e.g., silver thread) is used, a heating element thereof may be activated and controlled to coincide with skin surface temperatures and to optimize skin/muscle blood flow during periods of physiologic blood flow shunting.

An advanced compression garment may be provided with an onboard compression indicator, which may be equipped with means to indicate whether the advanced compression garment is applying a desired amount of pressure, or whether the pressure applied is too high or too low. For example, the compression indicator may be an electronic device having LED lights of different colors, with each color corresponding to one of the aforementioned pressure conditions. Alternative indicators may also be provided.

Output data from the sensor(s) may be communicated to a cloud-based server, a monitor or a combination monitor-controller. In one exemplary embodiment, a smart phone or similar device may be used as a monitor or monitor-controller, and may communicate via Bluetooth or another suitable technology with a transmitter or transceiver device that is connected to the sensors of the advanced compression garment. An application running on the smartphone or other data receiving device presents the sensor data to a user. The sensor data may be raw temperature and/or pressure readings, or the application may use or interpret the data to present another type of alphanumerical or graphical output. For example, the end user may be presented with pressure values in a static physiologic environment, or as a relative rate of pressure change over time during exercise.

When the sensor data receiving device is also a controller, the user may use the controller to set desired pressure levels, or to alter a set pressure level(s) such as when the activity level of the user might change and a higher pressure level is appropriate. An alert system may also be provided to alert the user that a desired pressure(s) or relative-rate of pressure change is not being achieved. In any embodiment, the user may be the wearer of the advanced compression garment and/or another party, such as a doctor, physical therapist, orthotist, etc., and any user may have the ability to observe real time pressures experienced by the wearer.

While it has been explained that exemplary advanced compression garments and advanced compression garments systems described herein are believed to be highly useful in mitigating exercise-related muscle injuries, the usefulness of such advanced compression garments is not so limited. For example, it is realized that exemplary advanced compression garment embodiments may find use in the medical field. One example of the medical field use of such an advanced compression garment is auto-regulated pressure application to the limb of an immobile or non-ambulatory patient to prevent deep vein thrombosis. Sequential compression could be implemented, for example, with the use of an appropriate motor or activated artificial muscle to provide gradual pressure changes.

Exemplary advanced compression garments and advanced compression garment systems may also be used intra-operatively to improve venous return in a patient under general anesthesia. Intermittent pressure changes producible with a motorized version of an exemplary advanced compression garment and advanced compression garment system may also be used to treat heart failure patients requiring end diastolic compression therapy to improve cardiac perfusion. High rates of compliance towards therapeutic intervention to lymphedema and chronic venous insufficiency in an outpatient setting can also be achieved.

Other medical uses are directly applicable to the advanced compression garment technology. For example, an inner layer with attached sensors may also function as a cast or splint liner to monitor pressures closest to the skin as overlying dressings are applied. This could assist with the alerting of excessive pressure to the skin/underlying muscle of the limb to which a cast is applied, thereby reduce human-related errors associated with too constrictively applying a bandage, cast, splint or dressing that may lead to skin breakdown or catastrophic muscle death (i.e., Volkmann's contracture). A sensor may be heat laminated to multiple different fabrics. Force sensing data may be observed over areas prone to excessive pressure leading to skin breakdown in multiple clinical scenarios; for example, along the hip, elbows, knees, occiput, etc., in the operating room theater, of bedridden patients, of post-surgical patients, of amputees wearing prosthetics, or in sedentary/paralyzed individuals all prone to decubitus ulceration.

Non-medical uses for exemplary advanced compression garments and advanced compression garment systems are also many. For example, an advanced compression garment may be worn during prolonged air travel so as to reduce edema caused by immobility at altitude. A compression sock may be added to the end of this compression sleeve to ensure that edema does not get pushed into the foot under this application. Advanced compression garments may also be applied to injured soldiers during long flights to a tertiary hospital because, at altitude, atmospheric pressure is much less than at sea level, and paired with an active inflammatory process following traumatic injury, edema changes can be excessive. Excessive edema or pressure to the tissue resulting from changes in altitude can in turn affect tissue perfusion, thus leading to increased infection rates or tissue loss.

As another example, athletes may wear an exemplary advanced compression garment during warm-up exercises to help prevent injury. The sensor information provided by an advanced compression garment may be used to design and implement a training regimen that optimizes competitive results. This may be achieved through the understanding of circulatory/perfusion states of muscles of interest during exercise to allow user notification of when and when not to maximally stress the muscle. Non-human applications may also mirror human applications, such as in horse racing to prevent injuries or monitor inflammation.

Other aspects and features of the exemplary embodiments will become further apparent to those skilled in the art upon review of the following detailed description of exemplary embodiments along with the accompanying drawing figures.

BRIEF DESCRIPTION OF THE DRAWINGS

In the following descriptions of the drawings and exemplary embodiments, like reference numerals across the several views refer to identical or equivalent features, and:

FIGS. 5A-5B illustrate various components of an exemplary finely adjustable and optionally motorized strap tensioning mechanism that may be used with exemplary advanced compression garments described and/or shown herein;

FIG. 9A schematically represents the various unassembled components of an exemplary sensor assembly construction of one exemplary advanced compression garment;

FIG. 9B schematically illustrates the components of FIG. 9A in an assembled state;

DETAILED DESCRIPTION OF THE EXEMPLARY EMBODIMENT(S)

Figure 1:
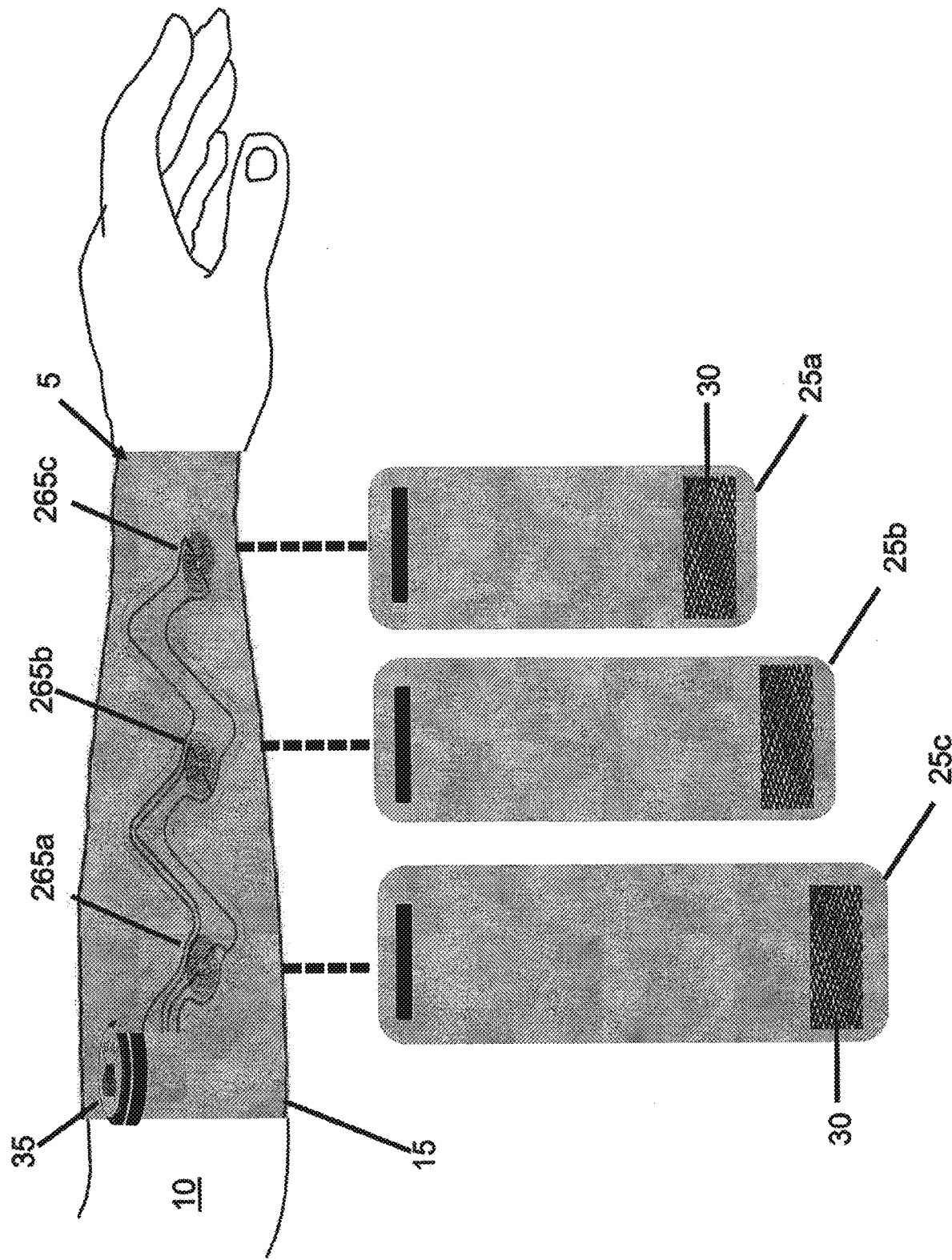
FIG. 1 illustrates one exemplary embodiment of an advanced compression garment in the form of a sleeve for application to a human arm.

One exemplary embodiment of an advanced compression garment in the form of a compression sleeve 5 designed to exert a compressive force on an arm 10 of a human wearer is illustrated in FIG. 1. The arm compression sleeve 5 may be used on an arm for various reasons. Non-limiting uses may include, for example, to treat swelling of the arm resulting from cancer-related resection or radiation treatment, or to provide information related to muscle status and/or performance during exercise.

The compression sleeve 5 may be of single layer or multi-layered construction. In the case of multi-layer construction, an inner layer 15 of material may act as a comfort layer that houses sensors 20a-20c of the compression sleeve 5, and also protects the underlying tissue of the arm 10 against any contour irregularity associated with the sensors. The inner layer 15 may be comprised of, for example but without limitation, a thin, soft and stretchy material such as polyester, spandex, lycra, nylon, neoprene, cotton, or various combinations thereof. The inner layer may be woven with silicone or other adhesives to provide diminished garment rotation, and/or silver or other conductive threads to provide heat transfer. The sensors 20a-20c of this embodiment, and other embodiments, may be embedded in or otherwise affixed to the inner layer 15 (or whatever layer is closest to the skin) such that the sensors will be located in close proximity to the skin of the wearer when the sleeve is worn.

Figure 15:
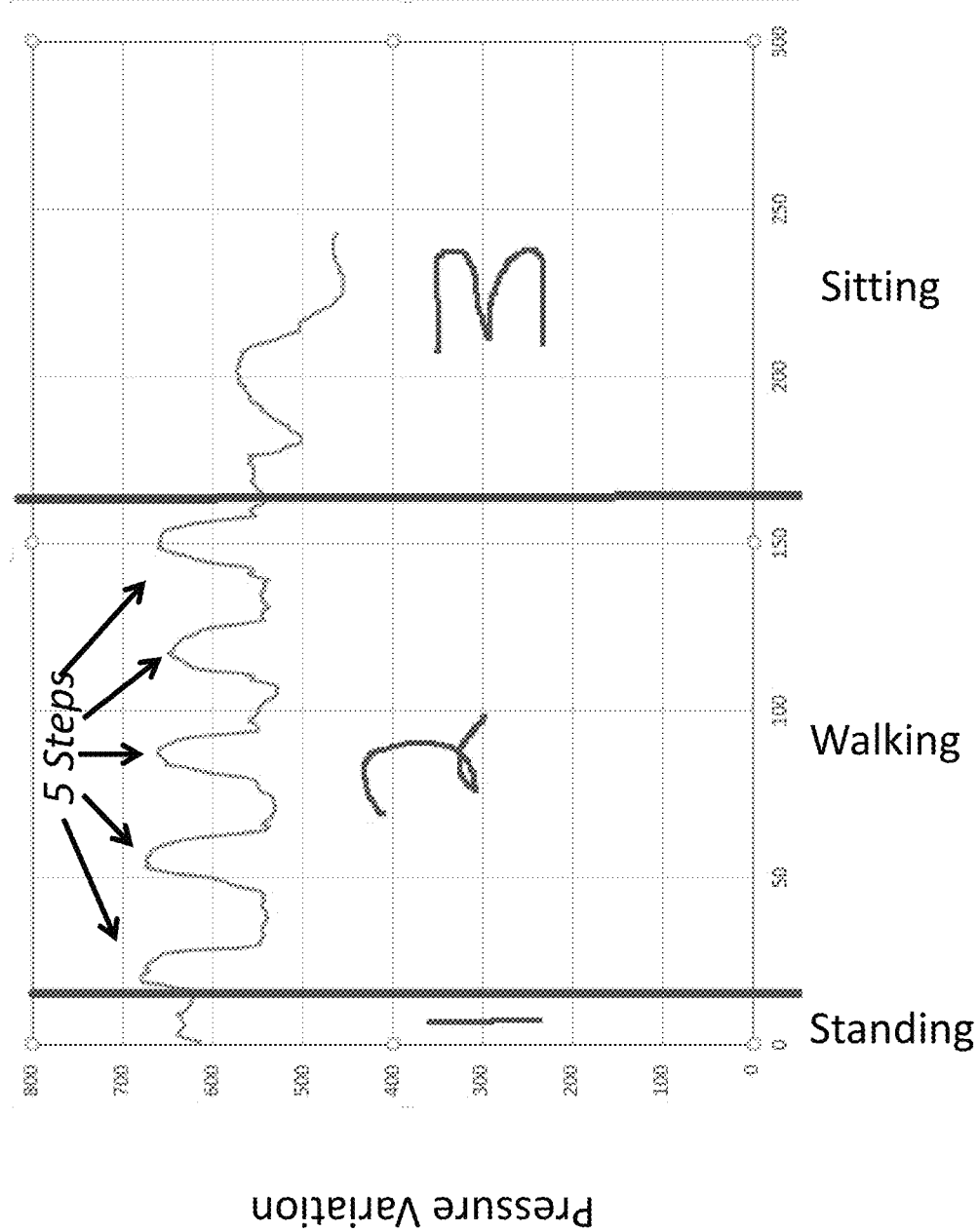
FIG. 15 graphically represents a type of sinusoidal compression (pressure) curve that typically occurs with muscle contraction as vessel dilation causes changes in pressures to the local tissue.

A multi-layered compression sleeve 5 will also include an outer layer that overlies the inner layer. The outer layer is preferably adapted to provide graded compression to the underlying limb musculature. To that end, the outer layer of this exemplary multi-layer compression sleeve 5 is divided into three individual straps 25a-25c of some width, that can be wrapped at least partially around the arm 10. The straps 25a-25c may be made of, for example but without limitation, polyester, nylon, neoprene, cotton, lycra, or any combination thereof. The straps 25a-25c may be removable (as shown) through the use of magnets, clasp mechanisms or the like. Alternatively, the straps may be permanently fixed to the inner layer 15, such as through the use of bonding (e.g., and adhesive), or via sewing, ultrasonic welding, etc. As described in more detail below and as is depicted in FIG. 15, such straps may also include synthetic or artificial muscle to provide transient or custom compressive forces.

The inner layer 15 of the compression sleeve 5 may also act to retain the compression sleeve on the arm 10 of the wearer at least until the compressive straps 25a-25c forming the outer layer of the sleeve are secured. Although not shown for purposes of clarity, the inner layer 15 may employ a zipper, small hooks, a hook and loop assembly (e.g., Velcro®), etc., to assist with sleeve retention. The fit provided by the inner layer 15 is preferably tight enough to prevent rotation of the compression sleeve 5, but not so tight as to contribute to the overall graded compression provided by the straps 25a-25c. In an alternative arm sleeve embodiment, the inner layer may also have a hand component to assist with comfort or increased positional preference.

When the exemplary compression sleeve 5 of FIG. 1 is donned, the sensors 25a-25c of the compression sleeve 5 target the mobile wad/flexor and extensor muscles of the forearm. Alternatively, the sleeve can extend up the arm or leg with sensor placement to target the deltoid/biceps or hamstring/quadriceps muscle groups in the arm and leg. It should also be noted that the straps 25a-25c are positioned to overlie the sensors 20a-20c when the straps are wrapped about the arm 10 and tightened.

It is desirable that the tightness of each strap 25a-25c be adjustable for the purpose of providing a proper amount of compression to the muscle underlying the given strap. In this manner, the straps 25a-25c may be used to provide an increasing (or otherwise varying) pressure gradient along the arm 10 so as, for example, to help push blood back to the heart in the venous system as well as the interstitium. Consequently, each strap 25a-25c of this exemplary compression sleeve 5 is provided with a portion 30 of a hook and loop (e.g., Velcro) fastening mechanism that engages a corresponding portion (not shown) thereof located on the outside of the inner layer 15 of the compression sleeve 5, or engages the inner layer itself. Other devices may be used to strengthen attachment of the straps to inner layer, such as but not limited to magnets and adhesive materials (e.g., silicone stippling).

As described in more detail below, an advanced compression garment such as the arm compression sleeve 5 may communicate with a monitor or monitor-controller for the purpose of transferring sensor data and possibly receiving instructions, etc. To that end, the compression arm sleeve 5 may also include a transmitter/transceiver device 35 that is in electrical communication with the sensors 20a-20c and serves as a communication bridge between the sensors and a monitor/monitor-controller. When the transmitter/transceiver device 35 is a transmitter only, the device is operative to receive and transmit sensor data to a monitor/monitor-controller. When the transmitter/transceiver device 35 is a transmitter and a receiver (i.e., a transceiver), the device is operative to receive and transmit sensor data to a monitor/monitor-controller and may also receive instructions or other information from a controller, such as for the purpose of setting or altering sensor pressure ranges, operating automatically operating a powered strap tensioning system (see FIGS. 5A-5B), etc. Communications between the transmitter/transceiver and monitor/monitor-controller may occur wirelessly, such as via Bluetooth® or other appropriate short-range communication technologies. The sensor(s) of a given advanced compression garment may also include built-in logic to facilitate communication and data transfer with a transmitter/transceiver.

Figure 2B:
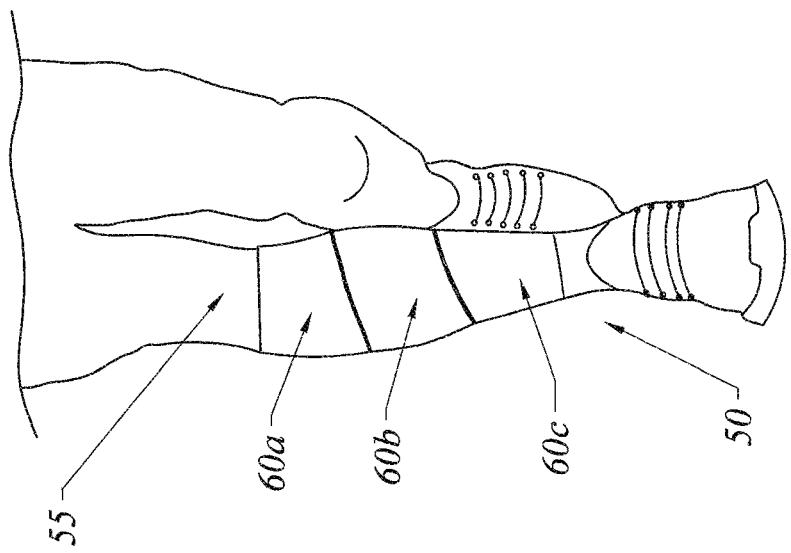
FIGS. 2A-2B illustrate an alternative exemplary embodiment of an advanced compression garment in the form of a sleeve for wearing on a human lower leg during exercise.
Figure 2A:
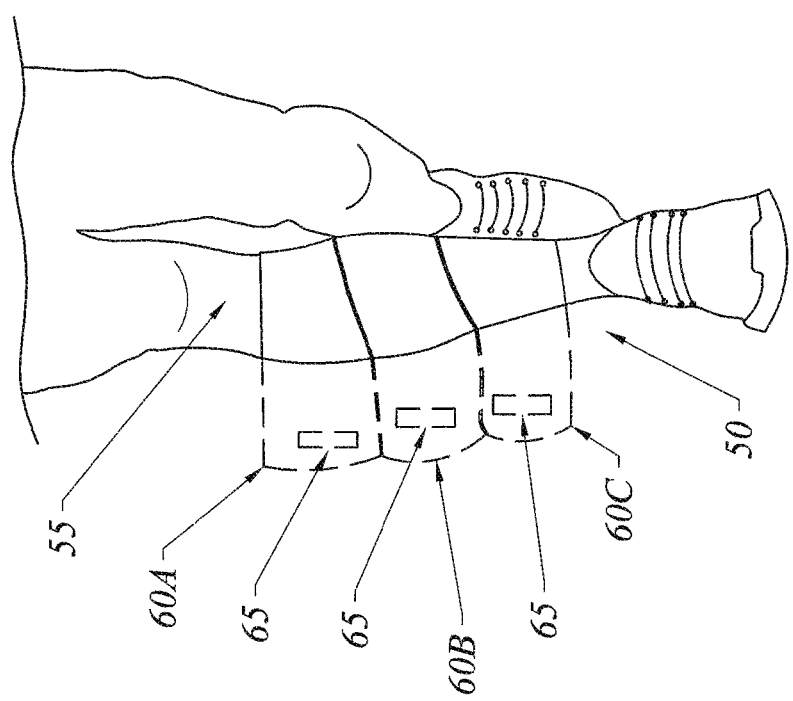

Another exemplary embodiment of an advanced compression garment in the form of a compression sleeve 50 designed to exert a compressive force on a lower leg 55 of a human wearer is illustrated in FIGS. 2A-2B. The leg compression sleeve 50 again includes an inner layer (not visible) and an outer layer in the form of three compressive straps 60a-60c, each provided with a closure 65, which may include a hook-and-loop or other fastening mechanism for securing the straps to the inner layer. The straps 60a-60c are shown in an unsecured position on the right leg of the wearer in FIG. 2A and in a secured and compressive position on the right leg of the wearer in FIG. 2B.

All of the other construction, donning, adjustment and functionality characteristics of the above-described arm compression sleeve 5 apply to the leg compression sleeve 50. It may be observed that, like the arm compression sleeve 5, the leg compression sleeve 50 is designed to target particular leg muscles when worn. In this particular exemplary embodiment, the leg compression sleeve 50 targets the calf/soleus/peroneus. Again, the sleeve and sensors may extend proximally up the leg.

Figure 3:
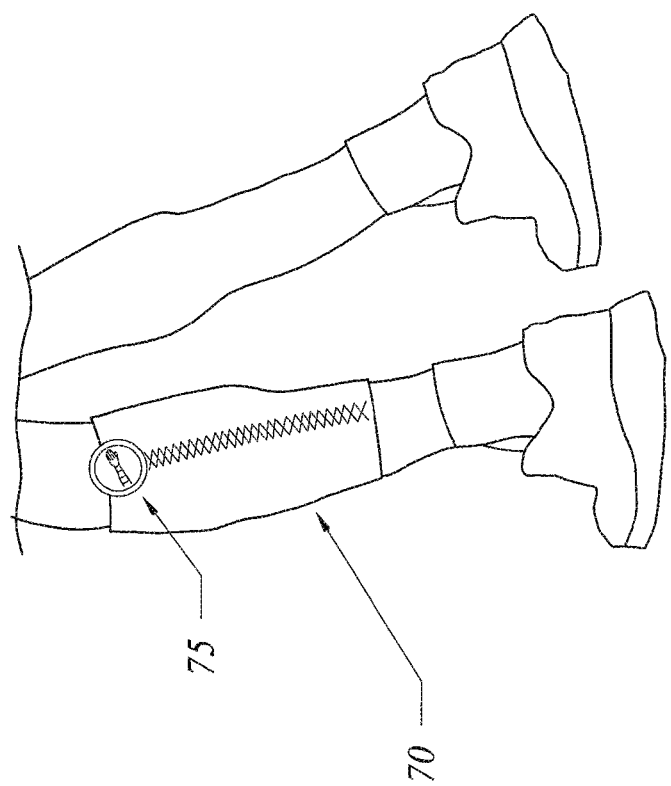
FIG. 3 indicates possible sensor locations for an exemplary compression sleeve such as that shown in FIGS. 2A-2B.

An alternative exemplary embodiment of a lower leg compression sleeve 70 is shown in FIG. 3. In this embodiment, the inner, mild compression garment layer of a multi-layer compression sleeve is used alone to monitor trends of relative pressure changes relating to muscle physiology during running exercise. A monitor or monitor-controller 75 is shown to be connected to sensors (not visible) of the sleeve 70. While not necessarily apparent in FIG. 3, sensors of the sleeve are located over both the anterior and posterior compartment of the lower leg when the sleeve is worn. In a variation of the sleeve embodiment of FIG. 3, a removable outer compressive layer (e.g., straps) may also be used, such as to optimize blood flow return during training, and then be removed prior to competition to reduce the overall weight of the sleeve 70. Such a sleeve embodiment may be used to create a customized pressure profile that may be applied to the leg. In addition to runners, such monitoring may also be beneficial to, for example, cyclists.

Figure 4B:
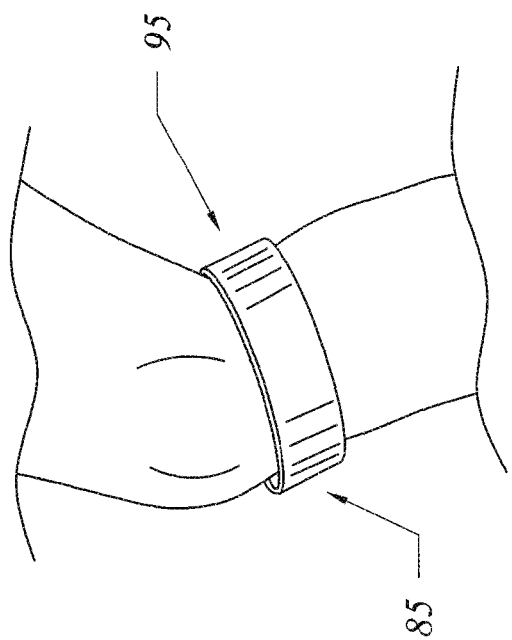
FIG. 4B illustrates another exemplary embodiment of an advanced compression garment in the form of a band for application near a human knee.
Figure 4A:
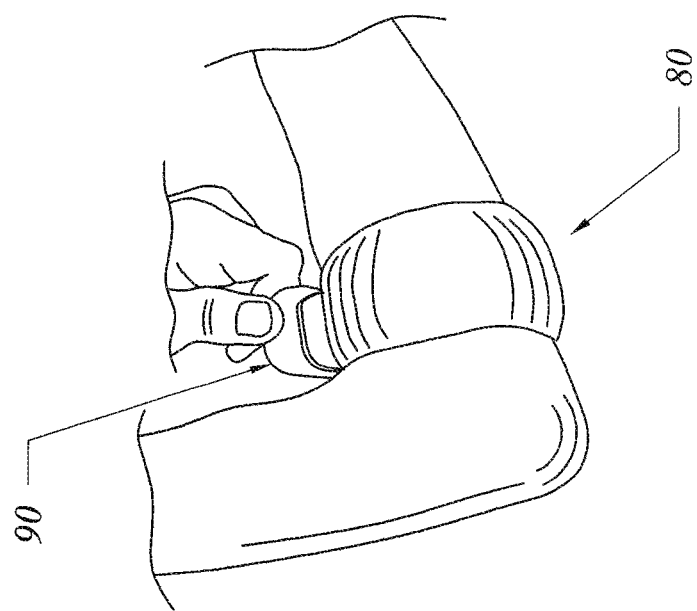
FIG. 4A illustrates another exemplary embodiment of an advanced compression garment in the form of a band for application near a human elbow.

Additional exemplary advanced compression garment embodiments are depicted in FIGS. 4A-4B. Particularly, FIG. 4A depicts a single sensor compression wrap 80 for application to a human arm, while FIG. 4B depicts a single sensor compression wrap 85 for application to a human leg. The arm compression wrap 80 may be used, for example and without limitation, to treat elbow pain, such as may be associated with tennis elbow. The leg compression wrap 85 may be used, for example and without limitation, as a patellar tendon brace or to treat leg pain, such as may be associated with shin splints or a hamstring strain/pull. In any case, the straps 90, 95 of the wraps 85, 90 are preferably designed so that, when multiple straps are present, there are no gaps between each strap so as to prevent any accumulation of fluid or edema between the straps. The pressure applied by the wraps 80, 85 may be in the range of 5-60 mmHg. All of the other construction, donning, adjustment and functionality characteristics of the above-described arm and/or leg compression sleeves 5, 50 may also apply to embodiments of the compression wraps 80, 85 of FIGS. 4A-4B.

In exemplary advanced compression garment embodiments, strap tension and, therefore, resulting strap compression, may be achieved in various ways. For example, securing a strap with a hook-and-loop fastener system (e.g., Velcro or the like) may provide gross pressure application. However, if a more accurate and repeatable application of pressure is desired, a more precise method of strap tensioning may be provided. An exemplary precision strap tensioning system 100 is represented in FIGS. 5A-5B for this purpose. In this exemplary embodiment, the strap tensioning system is comprised of several elements that may also be used independently to provide strap tension.

A first component of the strap tensioning system 100 is shown in FIG. 5A to be a reel and lace closure system 105. Such a reel and lace closure system is available from, for example, Boa Technology in Denver, Colo. Generally speaking, the reel and lace closure system 105 includes a reel 110 through which passes a lace 115 that may be incrementally wound around and retained by the reel. As shown in FIG. 5B, the lace may also be attached to one or more coupling elements, which in this case are hooks 120 or similar devices that may be attached to a strap 130 of an advanced compression garment. Rotation of a dial on the reel 110 either tightens or loosens the lace and correspondingly moves whatever is attached thereto. Coarse adjustments are possible with the reel and lace system 105, in comparison to the gross tension adjustments possible with the previously described Velcro strap securing system.

Also depicted as part of the exemplary strap tensioning system 100 is an optional motor 125, which may be an ultrasonic, piezoelectric, or other suitable motor capable of fine adjustment. When used, a drive shaft or other output of the motor 125 may be coupled to a dial of the reel 110, so as to provide powered operation of the reel and closure system 100. Finally, as shown in FIG. 5B, the hooks 120 that are coupled to the lace 115 of the reel and lace system 100 may be secured to a strap 130 of an exemplary advanced compression garment so as to provide tensioning thereof. When the motor 125 is coupled to the reel and lace system 105, tensioning may be powered, and possibly automatic in nature if the motor is coupled to a controller. Furthermore, use of such a motor 125 permits fine control over strap tension and the limb compression produced thereby.

Figure 6:
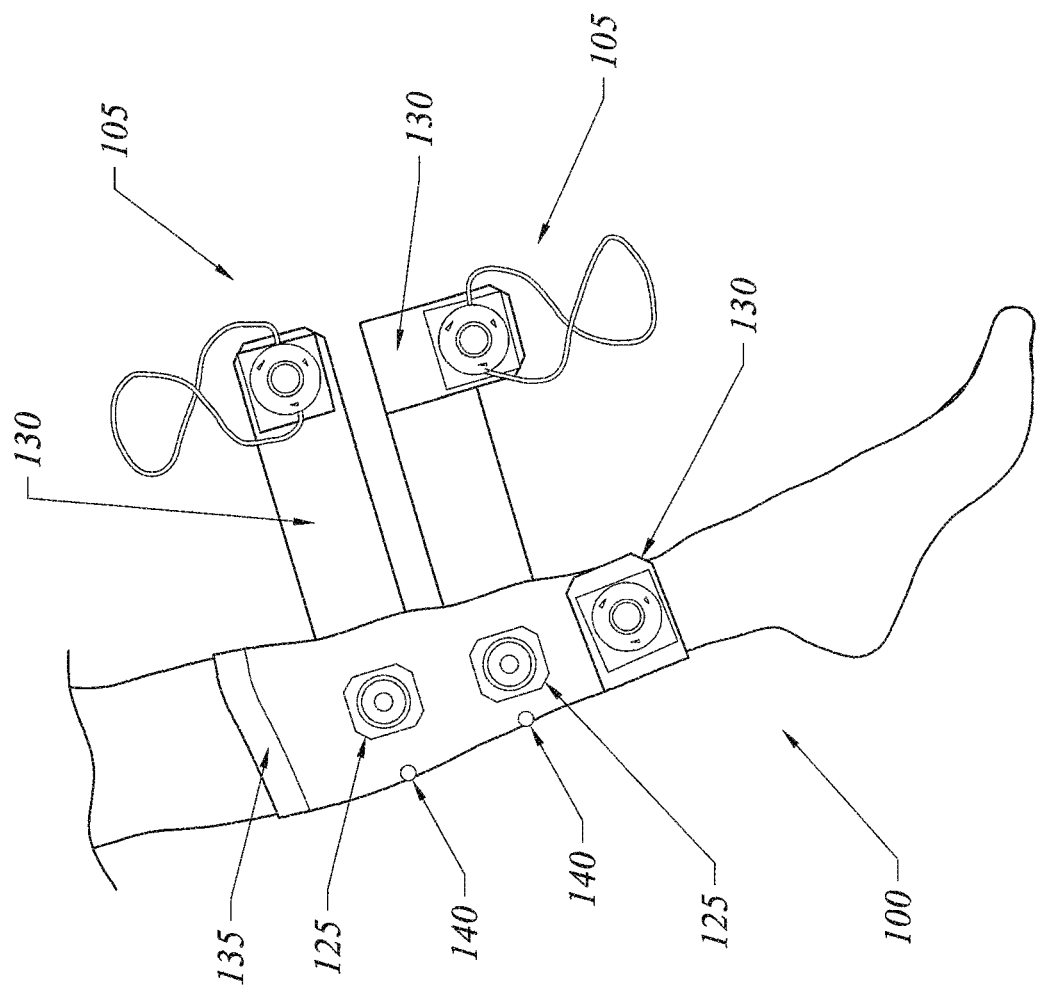
FIG. 6 depicts certain exemplary applications of the strap tensioning mechanisms of FIGS. 5A-5B.

FIG. 6 illustrates the use of three of the precision strap tensioning systems 100 of FIGS. 5A-5B on an exemplary lower leg advanced compression garment 135 having three sensors 140 (only two visible). In FIG. 6, the top two strap tensioning systems 100 are shown in an unsecured (non-tensioned) condition for purposes of illustration, whereas the bottom strap tensioning system 100 represents a tensioned strap 130 that overlies the third sensor. The straps 130 may be initially used to make gross compression adjustments, the reel and lace systems 105 may be used to make coarse compression adjustments, and the motors 125 may be added to the reel and lace systems and the straps 130 to make fine compression adjustments. When a motor 125 is used, automatic compression adjustments of as little as 1 mmHg may be made continuously or sequentially.

Figure 7B:
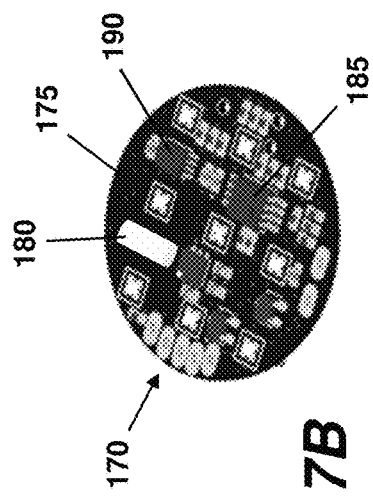
FIGS. 7A-7E schematically illustrate further details of an exemplary advanced compression garment transmitter/transceiver, such as the transmitter/transceiver shown in FIG. 1.
Figure 7C:
Figure 7D:
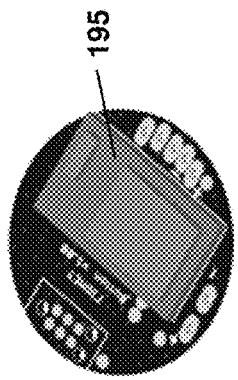
Figure 7E:
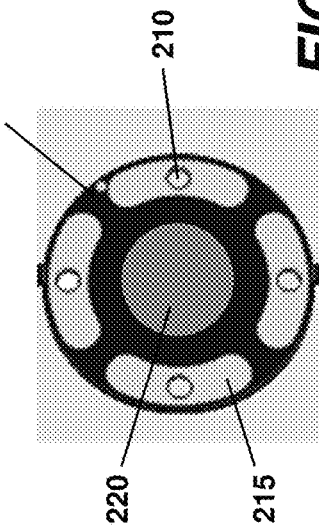
Figure 7A:
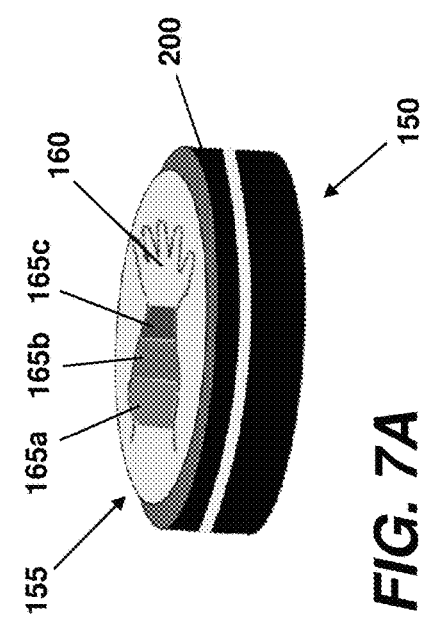

FIGS. 7A-7D schematically illustrate further possible functionality of an exemplary advanced compression garment transmitter/transceiver 150, such as the transmitter/transceiver shown in FIG. 1. Pressure indication using the transmitter/transceiver 150 is represented in FIG. 7A. In this regard, the transmitter/transceiver 150 is provided with a display 155 including a depiction of a human limb 160 (an arm in this case), which is divided into a number of different pressure zones 165a-165c relative to the number of individual pressure sensors and associated straps of an advanced compression garment (not shown) with which the transmitter/transceiver is in communication. Each of the zones 165a-165c may be independently illuminated to indicate whether the pressure applied to the corresponding area of the limb by the advanced compression garment during donning/application is within a predetermined range of pressures.

In the exemplary embodiment shown in FIG. 7A, each of the zones 165a-165c may be illuminated in blue, red or green, although other colors and combinations of colors may be used in other embodiments. In this case, blue indicates that an insufficient level of compression is being applied by the advanced compression garment, green indicates that a sufficient level of compression is being applied by the advanced compression garment, and red indicates that an excessive level of compression is being applied by the advanced compression garment. The pressure level indication associated with each color may, of course, be different in other embodiments. According to the color scheme used in the exemplary embodiment of FIG. 7A, the display indicates to a user that the advanced compression garment is applying too much pressure near the wrist of the wearer's arm, a proper amount of pressure in the area of the mid-forearm, and not enough pressure nearer the elbow. The tightness of the proximal and distal straps of the advanced compression garment may then be adjusted accordingly.

An alerting function may also be provided if the pressure applied or temperature sensed by an advanced compression garment drops below or exceeds some preset ideal pressure/temperature or range of pressures/temperatures. Alerts may be provided to the wearer and/or to a health care provider by way of the transmitter/transceiver, a connected monitor/monitor-controller (e.g., smart phone or other mobile device) or another device in communication with the sensors of the advanced compression garment.

Such a transmitter/transceiver device may be alternatively used with an advanced compression garment designed for monitoring purposes (see, e.g., the garment of FIG. 3) to indicate the physiologic state of the muscles over which the advanced compression garment is worn. In this case, the transmitter/transceiver display may be used to indicate the state of the muscle or the state of different muscle zones rather than the pressures applied by the compression garment to different zones along the length of the limb. For example, the color blue may be used to indicate that the underlying muscle is cold or prone to injury, the color green may represent a condition of maximal stress potential, and the color red may be used to indicate a required rest or cool down period. An indication may be provided that is representative of the general state of an entire muscle, or the display of the transmitter/transceiver may again be divided into zones that correspond to different areas of a muscle. The colors used to illuminate the display will correlate to slopes on a particular data set of pressure changes following perfusion pressures and shunting from exercise.

Alternative transmitter/transceiver embodiments may include displays that are useable by colorblind users. For example, an alternative color scheme may be provided for such a user. Similarly, audible tones, flashing lights, etc., may be used in addition to or in lieu of the illuminating colors described above.

Illumination of the zones 165a-165c of the transmitter/transceiver display 155 of FIG. 7A may be accomplished in a variety of ways that would be familiar to one of skill in the art. For example, light emitting diode (LED) technology may be used for this purpose. As shown in FIG. 7B, which presents a view of the internal electronics of the transmitter/transceiver 150 of FIG. 7A, a number of multi-color LEDs 170 are provided to illuminate the zones 165a-165c on the display 155 of the transmitter/transceiver 150. Proper illumination of the LEDs is accomplished based on commands from a microprocessor based on signals from the sensors associated with the advanced compression garment.

In addition to the illumination technology described above and/or other reporting or indicating functionality, an exemplary transmitter/transceiver may include various other electronic components. For example, as represented in FIGS. 7B-7E, an exemplary transmitter/transceiver may include one or more circuit boards 175, a power supply 180, a microprocessor 185 or microcontroller, memory 190, and wired or wireless communication devices, as well as any other components necessary to allow the transmitter/transceiver to receive data from the sensors of an advanced compression garment and to communicate with a monitor/monitor-controller. The particular transmitter/transceiver 150 of FIGS. 7A-7E includes a Bluetooth radio component 195 for providing wireless communication with a separate monitor/monitor-controller.

As indicated in FIG. 7A, the various electronic components of an exemplary transmitter/transceiver may be contained in a housing 200, which may be of various shapes and sizes, and may be manufactured from numerous materials such as but not limited to plastic, silicone, carbon fiber and other suitable materials. An exemplary transmitter/transceiver may be of water-resistant or waterproof construction.

A mechanism for facilitating electrical connection of an exemplary transmitter/transceiver to the sensor circuitry and sensors of an advanced compression garment may also be provided. This may be as simple as providing one or more jacks in the transmitter/transceiver for receiving the plug ends of wires connected to the sensors of the garment. In the exemplary embodiment of the transmitter/transceiver shown in FIG. 7E, however, a connecting face 205 along the bottom of the transmitter/transceiver is provided with a plurality of spring-loaded (i.e., pogo) pins 210 for facilitating electrical connection of the transmitter/transceiver 150 with the sensor circuitry of an exemplary advanced compression garment (as described in more detail below with respect to FIGS. 8A-8B). As shown, a metallic pad 215 may surround each pogo pin 210 to enhance the electrical connection or to simply serve as an alignment or mating mechanism. When present, the metallic pads 215 may be sized, located and arranged to align with conductive pads on a sensor assembly connector (as described in more detail below with respect to FIG. 10).

Releasable retention of an exemplary transmitter/transceiver on an exemplary advanced compression garment may be achieved in a number of ways that should be apparent to one of skill in the art. However, a novel concept for releasably retaining an exemplary transmitter/transceiver such as the transmitter/transceiver 150 of FIGS. 7A-7E is partially illustrated in FIG. 7E. More particularly, a magnet 220 is provided on the connecting face 205 of the transmitter/transceiver 150 to magnetically couple the transmitter/transceiver to a magnetic element of the sensor circuitry of an exemplary advanced compression garment (as is further described below with respect to FIG. 10). In this example, the magnet 220 is concentrically located between the pads 215 on the connecting face 205 of the transmitter/transceiver 150. The location of the magnet may be different in other embodiments.

Figure 8A:
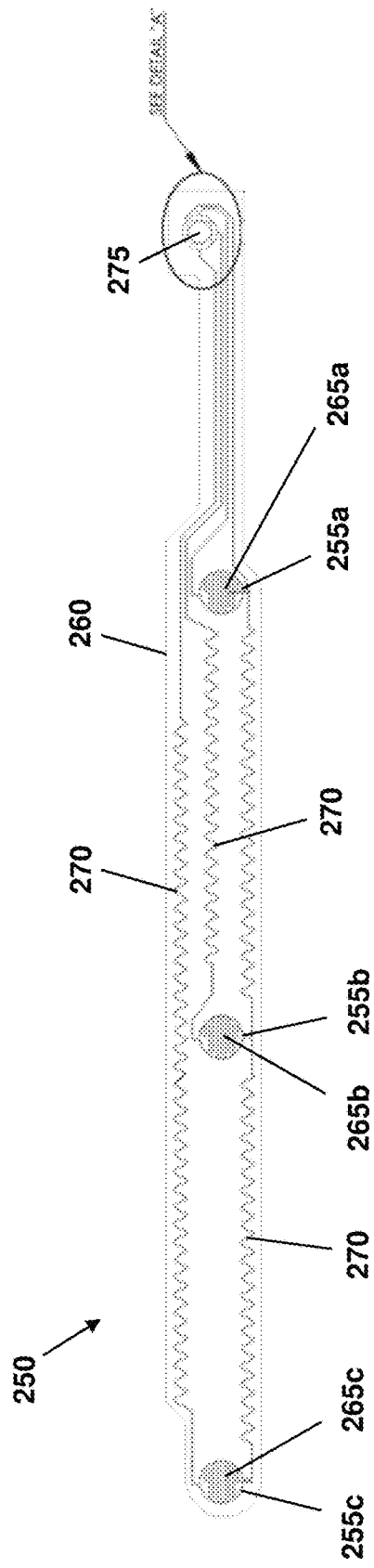
FIG. 8A schematically represents one portion of the circuitry layout of one exemplary flexible sensor assembly of an exemplary advanced compression garment.

FIG. 8A schematically represents the layout of exemplary sensor circuitry of a first portion 250 of one exemplary sensor assembly 350 (see FIG. 9B) of an exemplary advanced compression garment. This exemplary sensor assembly 350 includes various circuitry, which cooperates to produce the desired pressure and temperature readings during use of an associated advanced compression garment. The sensor assembly 350 may reside on the inner layer of an exemplary advanced compression garment, but other locations are also possible, as explained above.

The pressure sensors of the sensor assembly 350 may be force sensing resistors (FSRs), piezoelectric sensors, strain gauge sensors, near infrared spectroscopy (NIRS) sensors, or may be another sensor type known to one of skill in the art. The resistance of a FSR will vary in accordance with the amount of pressure that is applied to its sensing area. Therefore, a FSR is well-suited to measuring pressures and changes in pressure created by the wearing of an advanced compression garment. Furthermore, a FSR type sensor may require less than 5V to operate—meaning that power requirements are minimized.

In alternative embodiments, individual sensors may be replaced by an inner garment layer comprised of piezoelectric fabric, whereby the entire inner layer will be pressure and temperature sensing along the entirety thereof. Other sensing technologies may also be used, such as but not limited to, measuring resistance changes through woven silver threads as the threads are deformed. In any case, the sensor(s) or sensing layer will be placed in close proximity to the skin when the associated advanced compression garment is worn.

As shown in FIG. 8A, first sensor portions 255a-255c are arranged so as to be spaced apart along the length of the associated advanced compression garment. Consequently, the sensors are able to detect and report the pressures applied by the advanced compression garment, and/or the skin temperatures, at various locations along the length of the limb on which the garment is worn (as described above). The number of sensors utilized and the spacing between sensors may vary depending on, for example, the length of the advanced compression garment, the length of the limb on which the garment will be worn, and the number of different areas along the limb for which a pressure reading is desired.

While FSRs may be obtained in pre-existing form, the first sensor portions 255a-255c of this particular example may instead be created by printing on a substrate 260 using a conductive polymer or other conductive material in the form of an ink. When used, such an ink may be comprised of, for example, a conductive polymer such as but not limited to polyacetylene, polypyrrole, or polyaniline, or a piezoresistive substance. A suitable conductive ink may also be comprised of silver, silver chloride, carbon, or other materials that can be screen or laser printed onto substrates. An example of a latter type of such an ink is the CI-1036 silver ink distributed by Engineered Conductive Materials, in Columbus, Ohio. This ink is screen printable, comprised of a silver bimodal matrix, contains a highly elastic resin mix, and is very flexible and durable on a wide variety of substrates. The ink tracings for the sensors may vary depending on distance and need for greater stretchabliliy. A representative width may be, for example, 0.040" (1 mm) or thinner, at a thickness of, for example, 0.5 mil (12.5 µm).

The substrate of such an embodiment may be comprised of a variety of materials including but not limited to fabrics and plastic films. In the illustrated exemplary embodiment, the substrate 260 employed is a thin, flexible thermoplastic film. One such commercially available film is Bemis ST-604, available from Bemis International in Shirley, Mass. Generally speaking, Bemis ST-604 is a coextruded thermoplastic film supported on a carrier film providing a transport system to print onto stretchable fabric. The film may be composed of three layers: a barrier layer, that provides a temperature resistant printing surface needed to cure the conductive ink, an adhesive layer that permits bonding to the fabric, and a carrier layer that allows movement through a printing process. The ink may be coated on both sides to provide moisture resistance. The total thickness of an exemplary ST-604 film may be only about 0.0035 inches. Alternative films may include, for example, American Polyfilm VLM 4001, Eastex, Stedfast, Dow Corning (TPSiv), and Neenah.

Referring again to FIG. 8A, it can be observed that an active area (i.e., a pattern of conductors) 265a, 265b, 265c of each first sensor portion is printed, such as described above, onto the substrate 260. The active areas 265a, 265b, 265c are placed in electrical continuity with corresponding flexible electrical conduits 270 that may also be created by the printing thereof onto the substrate 260. The flexible electrical conduits 270 act as the leads that will carry signals produced by the assembled sensors 260a, 260b, 260c to a connector 275, which is adapted to couple the sensors to a transmitter/transceiver as described generally above and in more detail below.

The flexible nature of the electrical conduits 270 ensures that there is no increase in resistance across a connection or adapter between the conduits and sensors, nor a resultant loss of sensitivity at the sensor-circuit interface. The flexible nature of the electrical conduits 270 also eliminates any discomfort that might be imparted to a user if the conduits were comprised of metal wires and, unlike wires, are far less limiting on the elasticity possessed by the associated advanced compression garment.

Figure 8B:
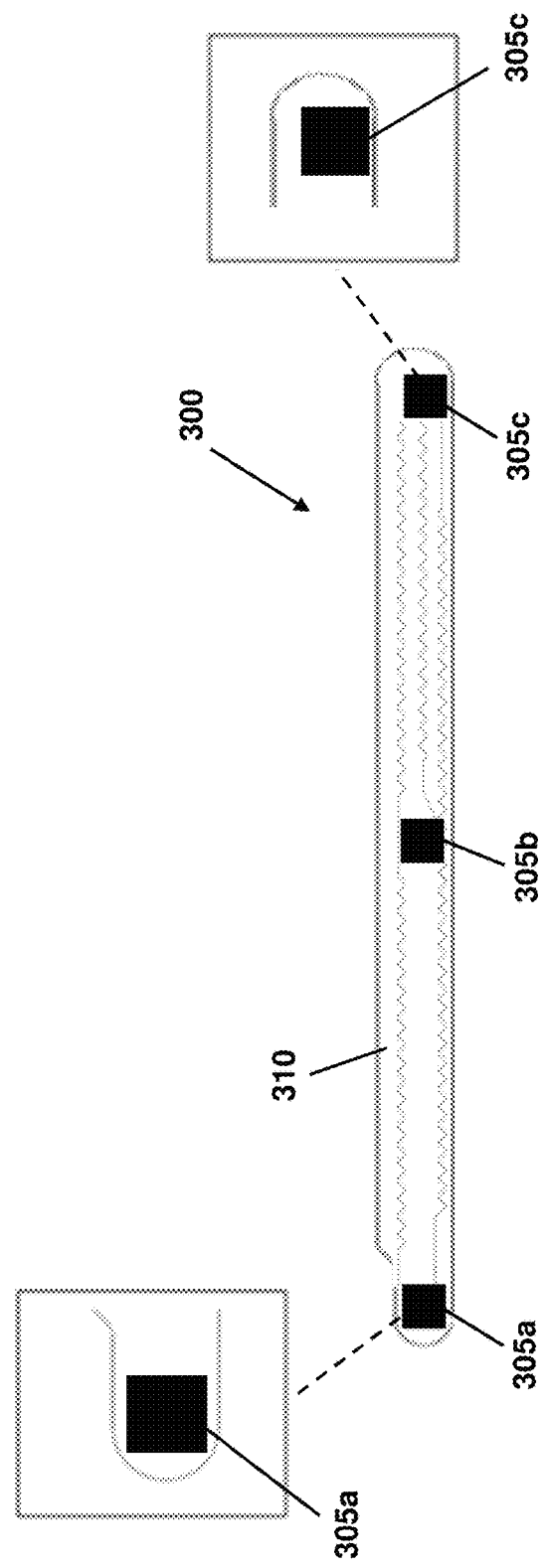
FIG. 8B schematically represents a corresponding second portion of the circuitry layout of the flexible sensor assembly of FIG. 8B.

A cooperating portion 300 of the provided exemplary sensor assembly 350 is schematically illustrated in FIG. 8B. As shown therein, a series of spaced apart receptor areas 305a, 305b, 305c are located on a second substrate 310, which may be of the same or a different composition as that of the first substrate 260. The receptor areas 305a, 305b, 305c are located and arranged on the second substrate 310 to correspond with the active areas 265a, 265b, 265c on the first substrate 260 upon assembly of the sensors (as described in more detail below). As with the active areas 265a, 265b, 265c and the electrical conduits 270 of the first portion of the sensor assembly, the receptor areas 305a, 305b, 305c may be printed onto the second substrate 310. Other known techniques for creating the receptor areas 305a, 305b, 305c on the second substrate 310 are also possible.

A better understanding of the assembled exemplary sensor assembly described and shown herein may be had by further reference to FIGS. 9A-9B. As may be observed therein, the first portion 250 and second portion 300 of the sensor assembly 350 are located to one another in a mirrored relationship such that the active areas 265a, 265b, 265c on the first substrate 260 and the receptor areas 305a, 305b, 305c on the second substrate 310 are aligned, in close proximity, and facing each other, to thereby form individual pressure sensors.

A separator layer 320 is located between the first substrate 260 and the second substrate 310. The separator layer 320 is of a thickness selected to produce an air gap 325 between the active areas 265a, 265b, 265c and corresponding receptor areas 305a, 305b, 305c of each pressure sensor when an associated advanced compression garment is in a relaxed (non-worn state). The air gap 325 ensures that the sensors will not produce pressure readings until the associated advanced compression garment is donned by a user and applies a pressure to the underlying limb tissue.

As illustrated in FIGS. 9A-9B, the separator layer material surrounds but does not intrude into the space between the active areas 265a, 265b, 265c and corresponding receptor areas 305a, 305b, 305c of each pressure sensor. The separator layer 320 may be comprised of a non-conductive foam, polyurethane, or other compressible material that will permit compression of the pressure sensors upon application of an associated pressure-sensing compression bandage to the limb/extremity of a user. The separator layer material may be air permeable and/or may be vented to permit the escape of any air trapped between the active areas 265a, 265b, 265c and corresponding receptor areas 305a, 305b, 305c of the pressure sensors upon compression thereof.

Once the various electrical components of the pressure sensors are printed or otherwise applied to the substrates 260, 310, the substrates may be die cut, laser cut, or otherwise trimmed if desired to minimize the size of the sensor assembly 350. It may also be possible to so dimension the substrates 260, 310 prior to applying the electrical components thereto.

Once the first portion 250 and second portion 300 of the sensor assembly 350 are properly arranged with respect to one another, with the separator layer 320 appropriately positioned therebetween, the adjacent faces of the substrates may be joined to produce a sealed, water-resistant sensor assembly. Joining of the substrates 260, 310 may be accomplished by any know technique, such as but not limited to, heat lamination. The sealed sensor assembly 350 may then be properly positioned on and attached to or embedded in a selected layer (e.g., the inner layer) of an associated advanced compression garment. For example, and without limitation, the sealed sensor assembly 350 may be attached to an inner layer of an advanced compression garment by heat laminating one of the substrates 260, 310 thereto.

In some exemplary embodiments of an advanced compression garment that employs FSR-type pressure sensors, an area of more rigid material (not shown) may be associated with one or both of the active and receptor areas of the FSR. For example, pieces of rigid material may be bonded to or embedded in the substrate(s) to overlie the active areas and/or receptor areas. When present, the rigid material may assist in transferring the compressive forces generated by the associated advanced compression garment to the pressure sensors.

In operation of the exemplary FSR pressure sensors subsequent to attachment to an associated advanced compression garment, donning of the advanced compression garment on a limb produces a compressive force that causes a compression of the separator material 320 and applies pressure to the pressure sensors. In the case of an advanced compression garment that employs FSR-type pressure sensors, this pressure produces contact between the active areas and receptor areas of the FSRs which alters the resistance thereof. Increased pressure will cause a greater portion of the active area to contact the receptor area of a given FSR, which further reduces the resistance of that FSR. Signals indicative of FSR resistance and changes in FSR resistance are received by a monitor/monitor-controller that is connected via a transmitter/transceiver to the sensor assembly and converted into pressure readings, as is described in more detail below in conjunction with FIGS. 12A-12B and 14A-14D.

In alternative embodiments, printed conductive material circuitry may be applied to a substrate or directly to a garment layer in a non-linear orientation/pattern, such that stretching of the associated layer of an advanced compression garment will not increase the resistance of the circuit, which could undesirably limit the sensitivity of the pressure sensors. Possible, but non-limiting conductive conduit patterns may include a ladder or grid pattern (i.e., horizontal and vertical printing) or a wavy or zig-zag pattern, to allow for stretch in both the horizontal and vertical directions while still permitting maximal conductive material-to-substrate contact.

Printed sensor elements may also be of various configuration and orientation. For example, the active and/or receptor areas of an exemplary FSR sensor may have interdigitating fingers, as shown in FIGS. 8A-8B. Likewise, the design of a given pressure sensor may be square, circular, wavy, or of another shape that helps the sensor to conform to the body part on which an associated advanced compression garment will be worn.

In an alternative embodiment, a FSR sensor may be placed on a dome composed of, for example, polyurethane or an equivalent or similar plastic polymer material, to replace the spacer layer of FIG. 9B while still providing a gap between the active and receptor elements of the FSR.

Figure 10:
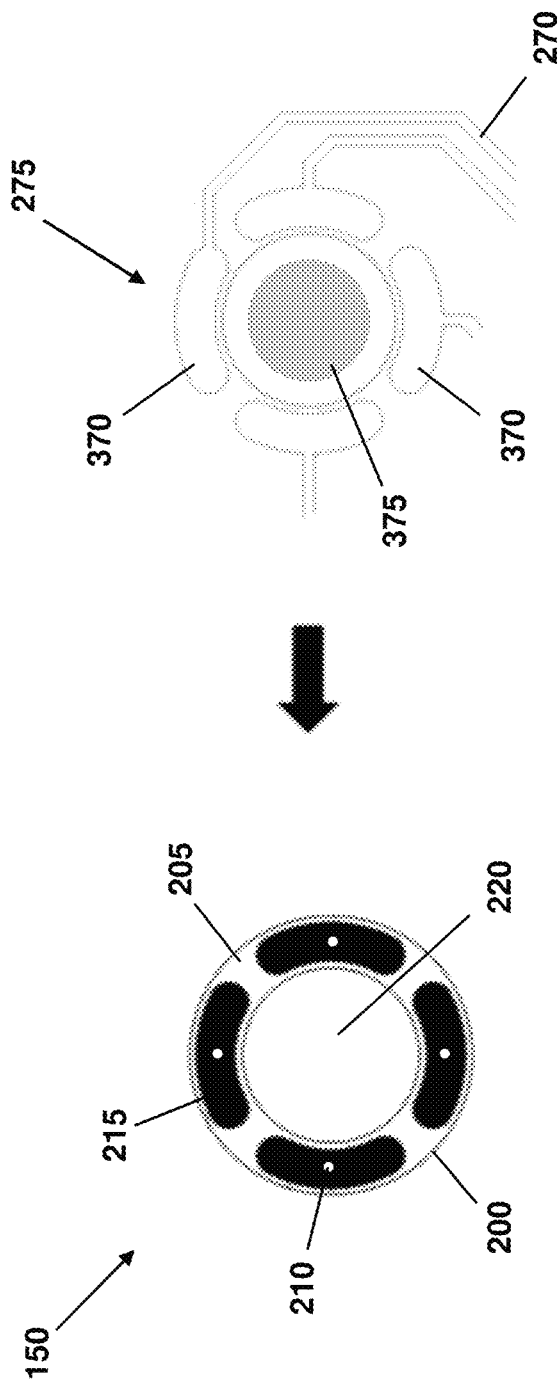
FIG. 10 schematically illustrates a connector portion of the sensor assembly portion depicted in FIG. 8A and its correspondence with a connecting portion of the transmitter/transceiver of FIGS. 7A-7E.

Referring back to FIG. 8A and also now to FIG. 10, it may be observed that the electrical conduits of the sensor assembly 350 terminate on a connector 275 having four pads 370 which, in this example, are printed silver ink pads that correspond to the three sensors of the sensor assembly, as well as a power connector. The power connector allows electrical energy from a power source within a transmitter/transceiver, etc., to be transferred to the sensors, while the remaining pads are used to receive and transfer data signals from the sensors to a transmitter/transceiver.

The connector 275 may be exposed on an associated advanced compression garment to facilitate electrical connection with an exemplary transmitter/transceiver. For example, and as represented in FIG. 10, an exemplary transmitter/transceiver 150 may be adapted in the manner shown in FIG. 7E to include connecting elements that are sized, located and arranged to engage the silver ink pads 370 of the sensor assembly connector 275 so as to provide an electrical connection between the sensor assembly and the transmitter/transceiver.

As discussed above—particularly with respect to FIG. 7E—releasable engagement between an exemplary transmitter/transceiver and the sensor assembly of an exemplary advanced compression garment may be maintained by magnets. To this end, the exemplary connector 275 is shown in FIG. 10 to be provided with a magnet 375 (or a ferrous element) to which a magnet of an exemplary transmitter/transceiver will be attracted. For example, the magnet 220 of the transmitter/transceiver 150 of FIGS. 7A-7E may couple with the magnet 375 of the connector 275 to releasably retain the transmitter/transceiver 150 on the associated advanced compression garment and in electrical connection with the sensor assembly 350. When present, the magnet or ferrous element 375 may be, for example and without limitation, sewn into or bonded to the fabric of the inner layer.

Figure 11:
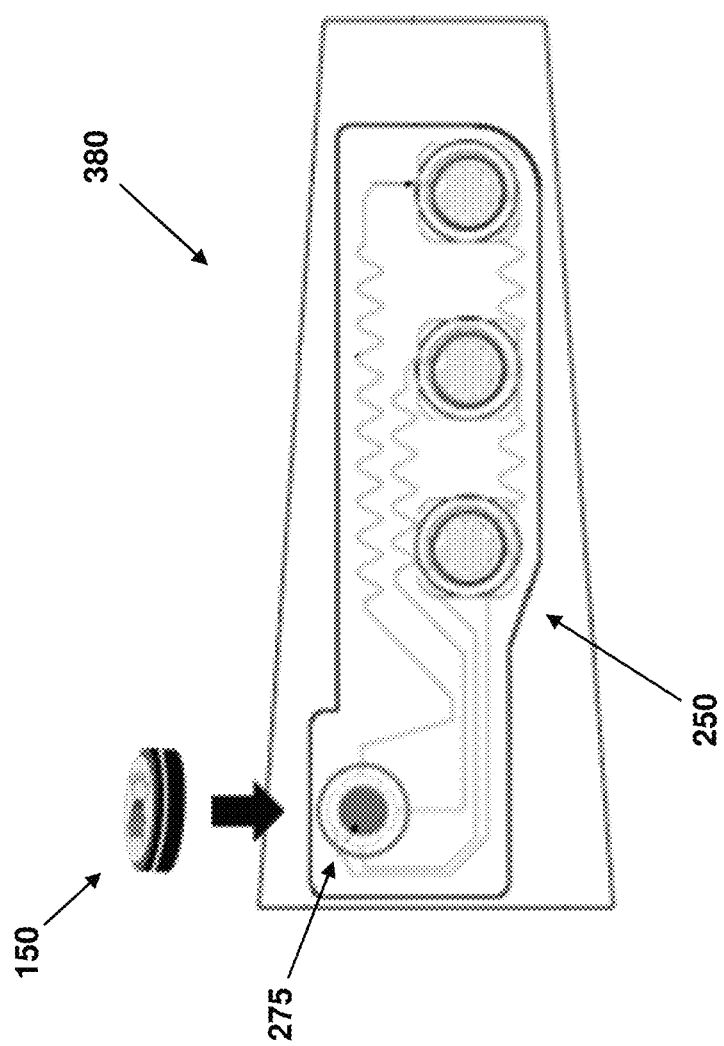
FIG. 11 depicts an exemplary flexible sensor assembly and an exemplary monitor or monitor-controller being used with an exemplary forearm compression sleeve.

A leg compression sleeve 380, which may be similar to the sleeve 50 of FIGS. 2A-2B or the sleeve 70 of FIG. 3, is generically depicted in FIG. 11 for purposes of further illustrating the releasable connection of an exemplary transmitter/transceiver to the sensor assembly of an advanced compression garment. The sleeve 380 is shown in FIG. 11 without an outer compression layer (e.g., straps) for purposes of clarity, but a compression layer may obviously be present. The leg compression sleeve 380 is shown to include the transmitter/transceiver 150 of FIG. 7A, and a sensor assembly including the sensor circuitry 250 illustrated in FIGS. 8A-8B. As may be observed, the connector 275 of the sensor circuitry 250 is exposed on the advanced compression garment to facilitate engagement by and electrical connection with the transmitter/transceiver 150. The transmitter/transceiver 150 may operate as described above.

Figure 12B:
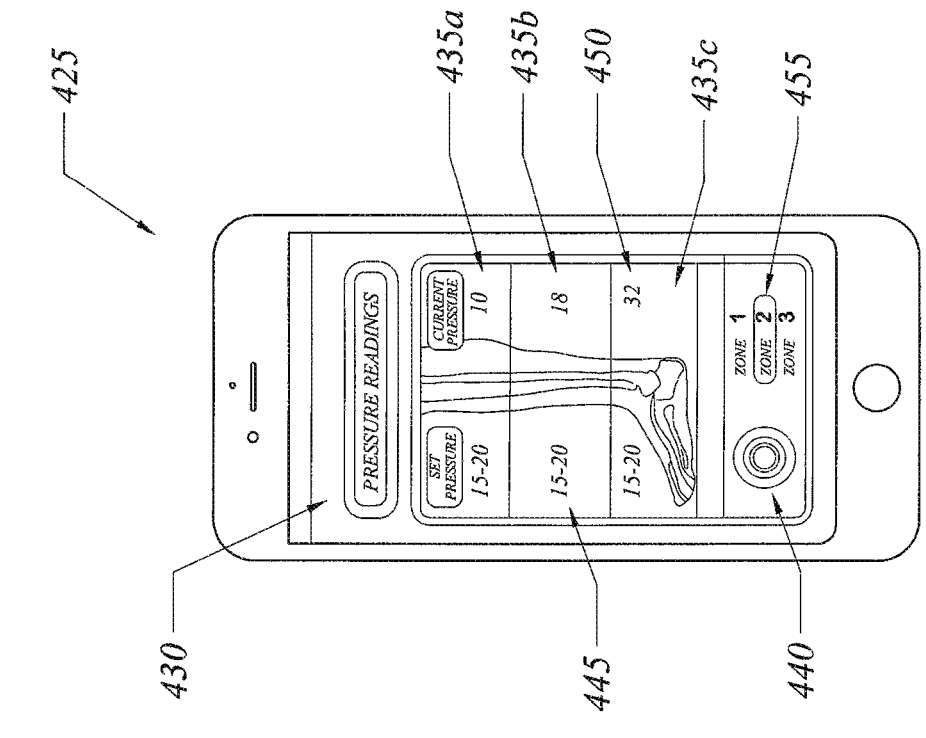
FIG. 12B shows and explains information presented by one exemplary display screen of an exemplary monitor or monitor-controller in the form of a smart phone that is receiving sensor data from the transmitter/transceiver of FIG. 12A.
Figure 12A:
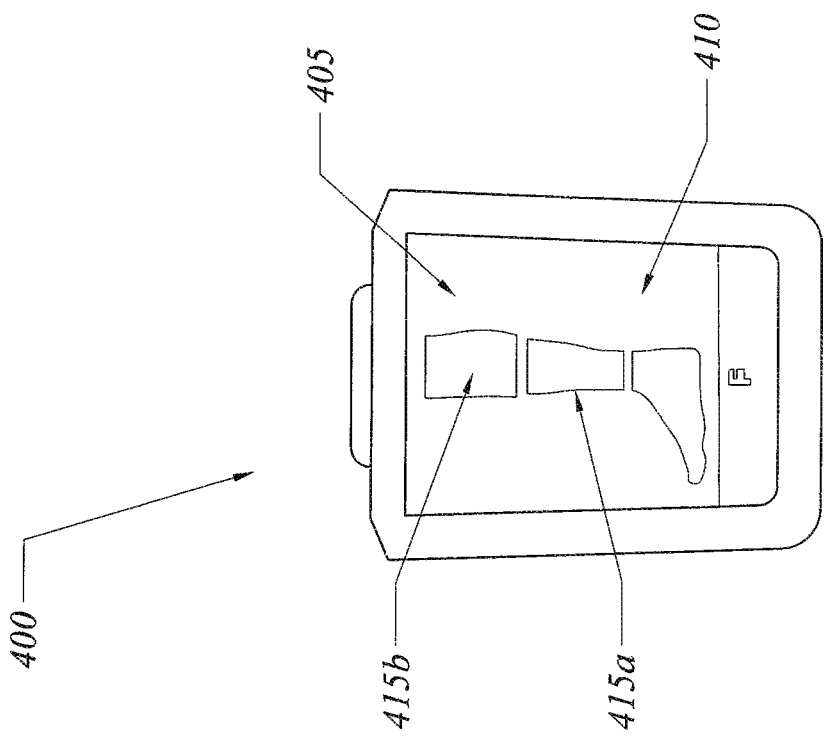
FIG. 12A depicts an exemplary display screen of another exemplary transmitter/transceiver for use with an exemplary advanced compression garment.

FIG. 12A depicts an alternative embodiment of a transmitter/transceiver 400 that may be used with an exemplary advanced compression garment. This particular transmitter/transceiver 400 again includes a display 405 with a depiction of a human limb 410 (a lower leg in this case), which is divided into a number of different pressure zones 415a-415b relative to the number of individual pressure sensors of an advanced compression garment (not shown) with which the transmitter/transceiver 400 is in communication. Each of the zones 415a-415b may again be independently illuminated to indicate whether the pressure applied to the corresponding area of the limb by the advanced compression garment during donning/application is within a predetermined range of pressures. The transmitter/transceiver 400 may further function in a like or similar manner to the transmitter/transceiver 150 described above.

One exemplary embodiment of a monitor/monitor-controller 425 that may be used with an exemplary advanced compression garment is represented in FIG. 12B. In this exemplary embodiment, a smart phone or similar device serves as the monitor/monitor-controller 425, with sensor communication occurring via a wired or wireless connection between the monitor/monitor-controller 425 and the transmitter/transceiver 400. Although the monitor/monitor-controller 425 is indicated in FIG. 12B as having both monitoring and controlling capabilities, it should also be realized that a monitor/monitor-controller may also function only as a monitor that receives and presents sensor data.

A specialized software application running on the monitor/monitor-controller 425 may be used to present the sensor data to a user via a display 430. The sensor data presented by the monitor/monitor-controller 425 may be raw temperature and/or pressure readings, or the associated software application may use or interpret the data to present another type of alphanumerical or graphical output. For example, the exemplary display 430 of the monitor/monitor-controller 425 of FIG. 12B is divided into three zones 435a-435c that indicate the amount of compression exerted by each of the three straps of an advanced compression garment with which the monitor/monitor-controller 425 is in communication. The sensor number (i.e., 1, 2 and 3) associated with the three straps of the advanced compression garment are identified along a lower portion 440 of the display, with desired pressure range values 445 associated with each sensor/strap appearing within the corresponding zone along the left side of the display and the actual pressure values 450 detected by each sensor/exerted by each strap appearing within the corresponding zone along the right side of the display. The number of the currently selected sensor is highlighted 455 along the bottom of the display 430, the settings of which may be edited via the monitor/monitor-controller 425.

Color may again be used on the monitor/monitor-controller 425 to help identify the compression status of each strap/sensor. For example, the zones 435a-435c may be highlighted in one of blue, red or green to indicate the compression level being provided by the advanced compression garment in each of the zones. In the exemplary display 430 of FIG. 12B, the first zone 435a is highlighted in blue to indicate that the pressure in said zone (i.e., 10 mm Hg) is less than the desired compression range of 15-20 mm Hg. Similarly, the pressure reading associated with the second zone 435b is highlighted in green to indicate that the pressure in said zone (i.e., 18 mm Hg) is within the desired compression range of 15-20 mm Hg. Lastly, the pressure reading associated with the third zone 435c is highlighted in red to indicate that the pressure in said zone (i.e., 32 mm Hg) exceeds the desired compression range of 15-20 mm Hg. The display and settings of a given embodiment may, of course, vary from the example shown.

Figure 13:
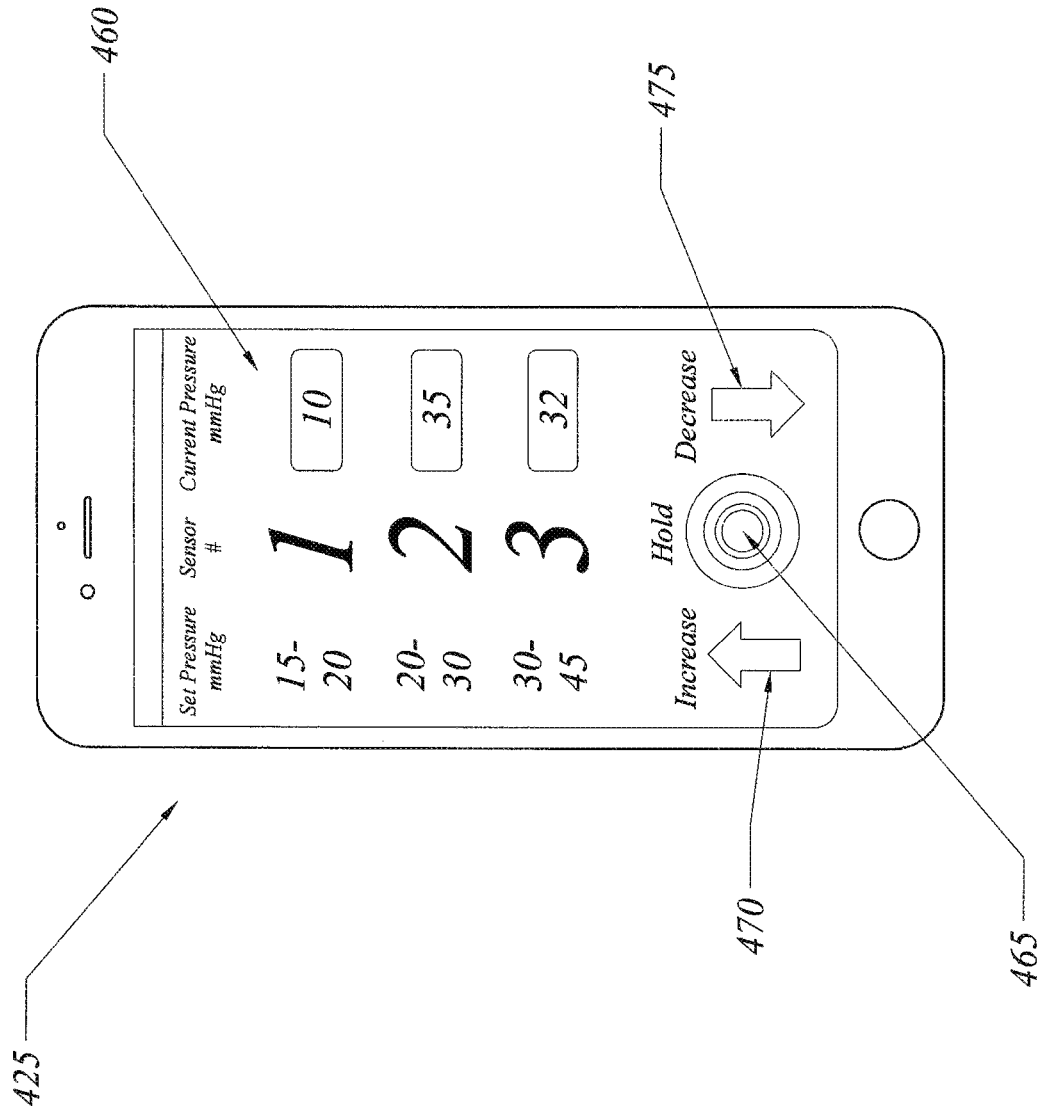
FIG. 13 illustrates another exemplary display screen of another exemplary monitor or monitor-controller that is receiving sensor data from an exemplary advanced compression garment.

When an exemplary monitor/monitor-controller, such as the monitor/monitor-controller 425, also includes control functionality, and the associated transmitter/transceiver includes receiver functionality, remote establishment and/or editing of pressure settings and/or other functions, and performance of other operations (e.g., operation of powered tensioning devices), is possible. Such remote control functionality is represented in FIG. 13 by another exemplary display screen 460 of the monitor/monitor-controller 425. For example, the display reveals a "Hold" button 465, a pressure "Increase" button 470 and a pressure "Decrease" button 475. These buttons may be used, for example, to manually alter strap tension on motorized advanced compression garment embodiments, or to change pressure settings (ranges) associated with a given advanced compression garment compression zone.

Figure 14D:
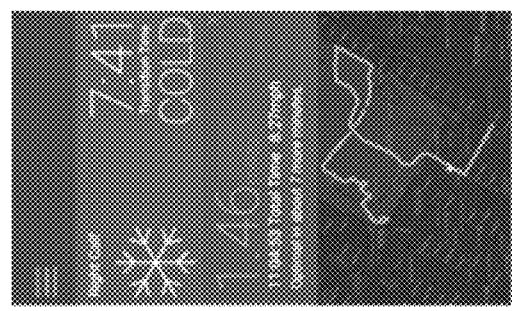
FIGS. 14A-14D illustrate additional exemplary display screens of an exemplary monitor or monitor-controller that is receiving sensor data from an exemplary advanced compression garment.
Figure 14C:
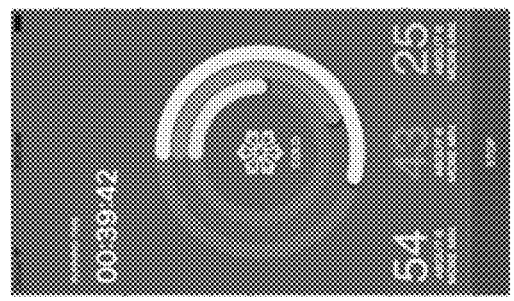
Figure 14B:
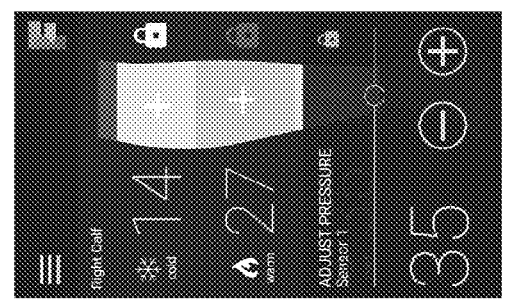
Figure 14A:
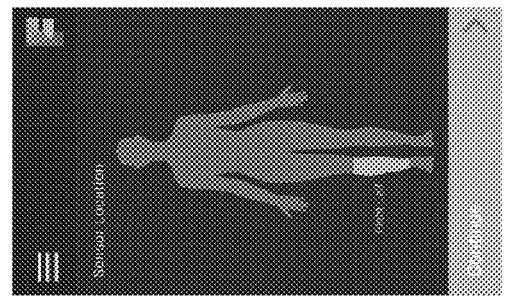

FIGS. 14A-14D illustrate additional exemplary display screens of an exemplary monitor/monitor-controller that may be used with an exemplary advanced compression garment. For example, FIG. 14A represents a basic display of information, such as perhaps a first display screen, which simply indicates to the user that the advanced compression garment from which readings are being received is located on the right calf of the user. The display of FIG. 14B indicates that the sensor nearest the user's foot (Sensor 1) is not reading properly, suggesting that the tightness of the advanced compression garment needs to be adjusted along that area of the user's limb. Temperatures and/or temperature changes along the advanced compression garment may also be displayed. The display of FIG. 14C is an alternative representation of temperature readings associated with a limb covered with an exemplary advanced compression garment. In this display, different temperature zones are indicated by arcuate bands of different colors. Numerical values representing real-time pressures with colors representing the functional zones of the muscle sensors being observed. Wait time values are also indicated. The display of FIG. 14D uses a colored zone (i.e., a blue zone in this case) to represent the functional state of muscles (i.e., cold in this case) and also provides a GPS representation of the particular course of a run taken by a wearer of an associated advanced compression garment.

As described above, an exemplary transmitter/transceiver may include a microprocessor, memory, communications elements, corresponding programming and/or software, and/or any other components necessary to produce the desired operation and interaction between the transmitter/transceiver, the sensors of an advanced compression garment, and a monitor/monitor-controller. Communication between a monitor/monitor-controller and a transmitter/transceiver associated with an advanced compression garment may be wired in nature, or may be wireless in nature such as via a short range communication technologies such as Bluetooth or Near Field Communications (NFC), or by other wireless communication technologies such as WiFi.

FIG. 15 graphically represents the type of sinusoidal compression (pressure) curve that typically occurs with muscle contraction as vessel dilation causes changes in pressures to the local tissue.

Figure 16B:
FIGS. 16A-16B collectively illustrate how temperature/pressure data from the sensor(s) of an exemplary advanced compression garment may be interpreted to notify a user that a monitored muscle has been sufficiently warmed up to be subjected to more intense exercise and when an appropriate cool down period has been completed.
Figure 16A:
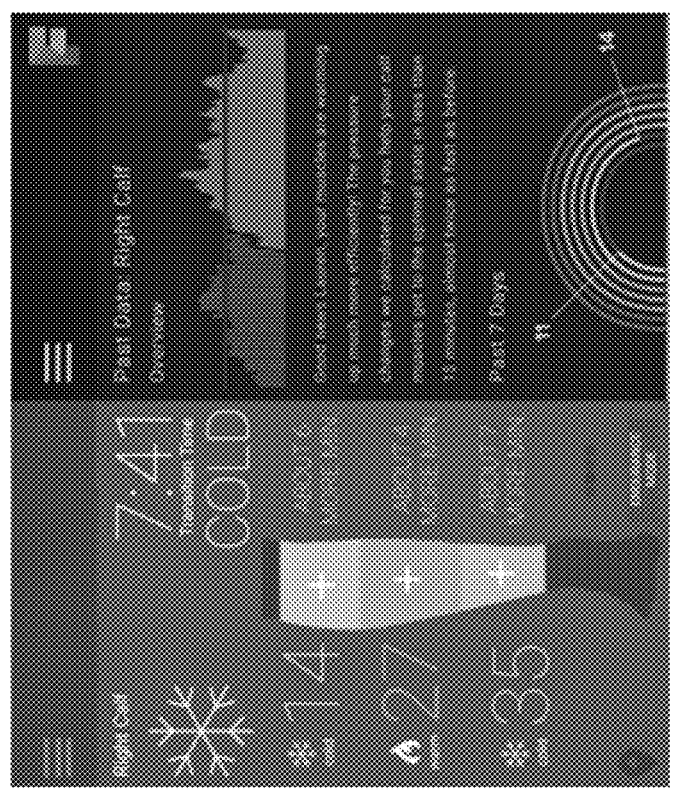

Since local heat stress causes increases in muscle blood flow, skin surface temperature may be used to detect and gauge an increase in muscle perfusion. Consequently, active skin surface temperature readings provided by an exemplary advanced compression garment may be used, for example, to inform the wearer or another party of the warmth of a muscle, which may indicate the readiness of the muscle to engage in more strenuous activity. In this regard, FIGS. 16A-16B illustrate how temperature/pressure data from the sensor(s) of an exemplary advanced compression garment may be interpreted for the purpose of notifying a user via an exemplary monitor/monitor-controller that a monitored muscle has been warmed up sufficiently to be subjected to more intense exercise.

Figure 17:
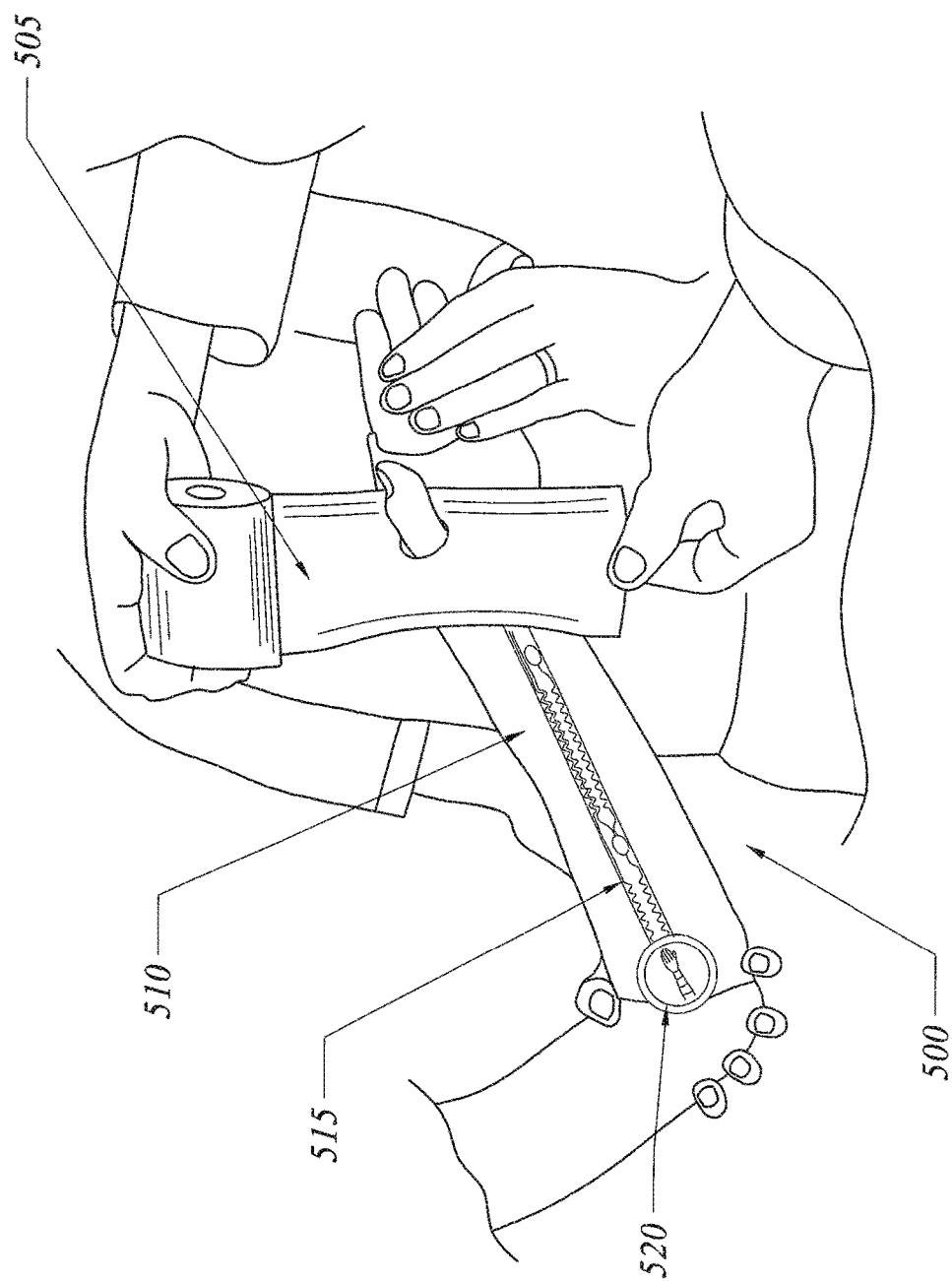
FIG. 17 illustrates how an exemplary garment in the form of a sensor-equipped cast liner may be used to assist in the appropriate application of overlying cast materials.

FIG. 17 illustrates how an exemplary advanced compression garment in the form of a sensor-equipped cast liner 500 may be used to assist in the appropriate application of overlying cast materials 505. As shown, the cast liner 500 includes a garment layer 510 to which is attached or embedded a sensor assembly 515. A transmitter/transceiver 520 is associated with the cast liner 500 and in communication with the sensor assembly 515. The construction and operation of the sensor assembly 515 and transmitter/transceiver 520, as well as the interaction therebetween and with a monitor/monitor-controller, may be as described above with respect to previously disclosed exemplary advanced compression garments.

Figure 18:
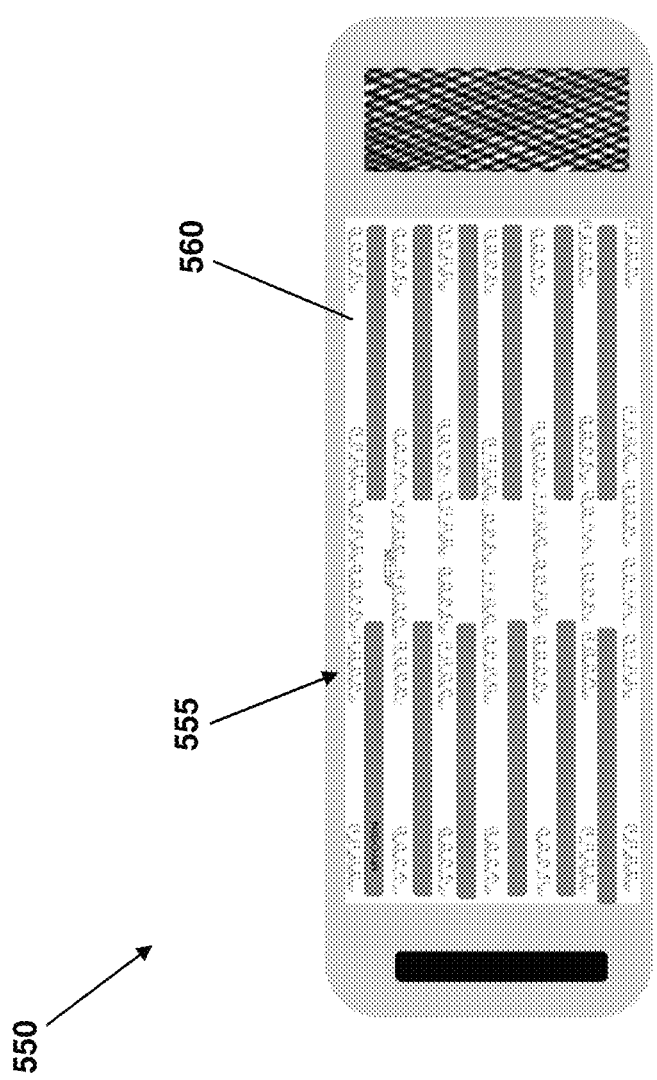
FIG. 18 schematically depicts an exemplary strap that includes artificial or synthetic muscle to allow an associated advanced compression garment to produce active compressive force changes.

FIG. 18 depicts an alternative embodiment of a compression strap 550 that may be used with exemplary advanced compression garments to produce active compression adjustments. In this strap embodiment, synthetic, artificial or mechanical muscle in the form of helical filaments, nano-tubules or similar structures may be used. These structures are intended to be similar to native "actin" in muscle anatomy. More particularly, as shown in FIG. 18, helical filaments, nano-tubules or similar structures 555 are anchored on a non-contractile capable polymer substrate 560. When an electric current is applied to the helical filaments, nano-tubules or similar structures 555, the structures will contract and, thus, shorten in overall length. With the helical filaments, nano-tubules or similar structures 555 properly oriented, the force of contraction may be used to adjust the level of compression level applied by an advanced compression garment to which the strap is attached. Such a strap may be designed to auto-contract (tighten) or auto-expand (loosen) based on an interpretation of pressures observed by the sensors of the associated advanced compression garment, so as to automatically arrive at a desired compression level. Activation of the strap 550 may be serial, sequential or intermittent in nature.

While it has been explained that exemplary advanced compression garments and advanced compression garments systems described herein are believed to be highly useful in mitigating exercise-related muscle injuries, the usefulness of such advanced compression garments is not so limited. For example, it is realized that exemplary advanced compression garment embodiments may find use in the medical field. One example of the medical field use of such a advanced compression garment is auto-regulated pressure application to the limb of an immobile or non-ambulatory patient to prevent deep vein thrombosis. Sequential compression could be implemented, for example, with the use of an appropriate motor to provide gradual pressure changes, such as is represented in FIG. 6. Piezoelectric, ultrasonic or similar motors may be used to automatically adjust the tension of the garment without user control. The end user may set a particular continual, sequential or graded pressure to be applied on the controller interface and the motors may adjust the tension of the straps to achieve the desired setting. This may be used for example in custom shoe lining, ski-boot lining, orthotic splint lining (to loosen or tighten when edema changes), or legs during and post-surgery. In this embodiment, the purpose of the automatic function is to prevent too tight or too loose fitting in order to maximize user compliance rates.

Other configurations and uses of exemplary advanced compression garment embodiments are also possible, as discussed previously. Also, the sensors described in the embodiments may further be applied in various medical scenarios. The pressure sensors may be added to compression garments that are used for burn victims when treating hypertrophic scarring. For example, facial scarring is treated with a hard plastic face mask to apply pressure. It is thought that scarring is reduced by lowering the oxygen content of the scar tissue. The sensors may be placed in multiple locations to ensure even application of pressure across the non-linear facial features. The thin lining with the sensors may be placed in the operating theater to monitor areas that are prone to ulceration from inadequate pressure relief (i.e., ischium/gluteal surface, elbows, heels, face in prone position).

REFERENCES

1. Jacobson, Jason. "2015 State of the Sport—U.S. Race Trends|Running USA." 2015 State of the Sport—U.S. Race Trends|Running USA. Running USA, 13 Jul. 2015. Web. 9 Sep. 2015.
2. Darabaneanu S, Overath C H, Rubin D, Lüthje S, Sye W, Niederberger U, Gerber W D, Weisser B. Aerobic exercise as a therapy option for migraine: a pilot study. Int J Sports Med. 2011 June; 32(6):455-60.
3. Van Mechelen W. Running injuries. A review of the epidemiological literature. Sports Med. 1992 November; 14(5):320-35.
4. Shamus J, Shamus E. The Management of Iliotibial Band Syndrome with a multifaceted approach: A multifaceted approach: A double case report. Int J Sports Phys Ther. 2015. June; 10(3):378-90.
5. Schmikli S L, de Vries W R, lnklaar H, Backx F J. Injury prevention target groups in soccer: injury characteristics and incidence rates in male junior and senior players. J Sci Med Sport. 2011 May; 14(3):199-203.
6. Mohib M, Moser N, Kim R, Thillai M, Gringmuth R. A four year prospective study of injuries in elite Ontario youth provincial and national soccer players during training and matchplay. J Can Chiropr Assoc. 2014 December; 58(4):369-76.
7. Hassabi M, Mortazavi M J, Giti M R, Hassabi M, Mansournia M A, Shapouran S. Injury profile of a professional soccer team in the Premier League of Iran. Asian J Sports Med. 2010; 1(4):201-208.
8. Barcroft H, Edholm O G. The effect of temperature on blood flow and deep temperature in the human forearm. J Physiol (Lond) 102: 5-20, 1943.
9. Barcroft H, Bonnar W M, Edholm O G. Reflex vasodilatation in human skeletal muscle in response to heating the body. J Physiol 106: 271-278, 1947.
10. Pearson J, Low D A, Stöhr E, Kalsi K, Ali L, Barker H, Gonzalez-Alonso J. Hemodynamic responses to heat stress in the resting and exercising human leg: insight into the effect of temperature on skeletal muscle blood flow. Am J Physiol Regul Integr Comp Physiol. 2011 March; 300(3).
11. Gonzalez-Alonso J, Mortensen S P, Jeppesen T D, Ali L, Barker H, Damsgaard R, Secher N H, Dawson E A, Dufour S P. Haemodynamic responses to exercise, ATP infusion and thigh compression in humans: insight into the role of muscle mechanisms on cardiovascular function. J Physiol 586: 2405-2417, 2008.
12. Minson C T, Wladkowski S L, Cardell A F, Pawelczyk J A, Kenney W L. Age alters the cardiovascular response to direct passive heating. J Appl Physiol 84: 1323-1332, 1998.
13. Rodrigues R, Baroni B M, Pompermayer M G, de Oliveira Lupion R, Geremia J M, Meyer F, Vaz M A. Effects of acute dehydration on neuromuscular responses of exercised and nonexercised muscles after exercise in the heat. J Strength Cond Res. 2014 December; 28(12): 3531-6.
14. Maughan R J. Distance running in hot environments: a thermal challenge to the elite runner. Scand J Med Sci Sports. 2010 October; 20 Suppl 3:95-102.
15. Bieuzen F, Brisswalter J, Easthope C, Vercruyssen F, Bernard T, Hausswirth C. Effect of wearing compression stockings on recovery after mild exercise-induced muscle damage. Int J Sports Physiol Perform. 2014 March; 9(2):256-64.

While certain exemplary embodiments are described in detail above the scope of the general inventive concept is not to be considered limited by such disclosure, and modifications thereof are possible without departing from the spirit of the invention as evidenced by the following claims:

What is claimed is:

1. An advanced compression garment for donning over a limb, a head or a torso of a wearer, comprising:
    an inner layer encircling skin of a portion of the limb, the head or the torso; the inner layer including at least one sensor in close proximity to the skin for sensing magnitude of compression of the advanced compression garment against the skin and underlying muscle;
    a connector attached to the inner layer and communicating with the at least one sensor; the connector distinct from the inner layer and adapted to hold either a transmitter or a transceiver; the transmitter or transceiver comprising a housing including a first display on a first side and an opposed connecting face held by and in contact with the inner layer; the connecting face including magnetic tabs for attraction with the inner layer, wherein the transmitter or transceiver is releasably connected to the connector and the inner layer, adapted to communicate with the at least one sensor and communicate wirelessly with a monitor or monitor-controller remote from the inner layer;
    the first display displaying first indications of pressure applied to the skin by the advanced compression garment;
    a second display of second indications of pressure applied to the skin displayed by the monitor or monitor-controller; the monitor's or monitor-controller's second display distinct from the first display; and
    an outer compressive layer adapted for contacting the inner layer and applying pressure to the skin.

2. The advanced compression garment of claim 1, wherein:
    the first indications include a depiction of a human limb.

3. The advanced compression garment of claim 2, wherein the at least one sensor is a plurality of sensors, wherein: the second indications include a depiction of a human limb divided into a number of zones, each zone corresponding to a sensor of the plurality of sensors of the advanced compression garment; and
    wherein the monitor or the monitor-controller is adapted to apply any of several colors to each zone depending on a pressure condition indicated by the sensor of the plurality of sensors associated with the given zone.

4. The advanced compression garment of claim 3, wherein the monitor or the monitor-controller includes control functionality by which settings and functions of the advanced compression garment may be manipulated.

5. The advanced compression garment of claim 1, wherein the at least one sensor is a plurality of sensors, wherein the first indications are divided into a number of zones, each zone corresponding to a sensor of the plurality of sensors of the advanced compression garment.

6. The advanced compression garment of claim 1, wherein the transmitter or the transceiver communicates via a wireless communication technology.

7. The advanced compression garment of claim 6, wherein:
- the monitor or the monitor-controller is a device selected from the group consisting of a programmed smart phone, tablet, smart watch, smart device and computer; and
- the monitor/monitor-controller includes specialized software that is usable to analyze and display sensor data.

8. The advanced compression garment of claim 1, wherein the at least one sensor is selected from the group consisting of a force-sensing resistor, a piezoelectric sensor, a strain gauge sensor, and a near infrared spectroscopy sensor.

9. The advanced compression garment of claim 8, wherein the at least one sensor is a piezoelectric fabric.

10. The advanced compression garment of claim 1, wherein the at least one sensor is a force-sensing resistor that is printed on a substrate or a garment layer.

11. The advanced compression garment of claim 10, wherein the force-sensing resistor is printed from a material selected from the group consisting of a conductive polymer, a piezoresistive substance, and carbon.

12. The advanced compression garment of claim 10, wherein the force-sensing resistor is printed from a conductive silver ink on a substrate of coextruded thermoplastic film.

13. The advanced compression garment of claim 10, further comprising at least one flexible electrical conduit printed on the substrate, wherein the at least one sensor communicates with the connector.

14. The advanced compression garment of claim 13, wherein the connector includes:
- a first conductive pad adapted to transfer electrical energy via the at least one flexible electrical conduit to the at least one sensor; and
- a second conductive pad adapted to transfer data signals received from the at least one sensor via the at least one flexible electrical conduit to the transmitter or the transceiver.

15. The advanced compression garment of claim 1, wherein the at least one sensor is also adapted to sense and report skin surface temperature.

16. An advanced compression garment for donning over a limb, a head or a torso of a wearer, comprising:
- an inner layer encircling a portion of skin of the limb, the head or the torso and positioned to be in contact with the skin of the wearer;
- a sensor assembly including a series of spaced apart pressure sensors in close proximity to the skin for sensing a magnitude of compression of the advanced compression garment against the skin; the series of spaced apart pressure sensors distributed along a length of the inner layer;
- an outer compressive layer in the form of a plurality of adjacent straps, the number of straps corresponding to a number of the sensors, each strap attached at one end to the inner layer and adapted for at least partial wrapping under tension around the skin;
- a connector attached to the inner layer and communicating with the sensor assembly; the connector, distinct from the inner layer, holding either a transmitter or a transceiver; the transmitter or transceiver comprising a housing including a first display on a first side and an opposed connecting face held by and in contact with the inner layer; the connecting face including magnetic tabs for attraction with the inner layer, wherein the transmitter or transceiver is releasably connected to the connector and the inner layer, adapted to communicate with the sensor assembly and communicate wirelessly with a monitor or monitor-controller remote from the inner layer;
- the first display displaying first indications of pressure applied to the skin by the advanced compression garment; and
- a second display of second indications of pressure applied to the skin displayed by the monitor or monitor-controller; the monitor's or monitor-controller's second display distinct from the first display.

17. The advanced compression garment of claim 16, wherein the sensors and straps are arranged such that the sensors will underlie the straps when the straps are placed in tension and secured.

18. The advanced compression garment of claim 16, wherein the sensor assembly further comprises:
- a first portion including active sensor areas and flexible electrical conduits conductively connecting the sensors to the connector, the active sensor areas, and conduits comprised of conductive ink printed onto a first thermoplastic substrate;
- a cooperating second portion including receptor areas corresponding in number and location to the active sensor areas on the first portion, and flexible electrical conduits conductively interconnecting the receptor areas, the active sensor areas and conduits comprised of conductive ink printed onto a second thermoplastic substrate;
- the first portion and the second portion located to one another in a mirrored relationship such that the active areas on the first substrate and the receptor areas on the second substrate are aligned, in close proximity, and facing each other, so as to form individual pressure sensors; and
- a separator layer located between the first substrate and the second substrate, the separator layer being of a thickness sufficient to produce an air gap between the active sensor areas and corresponding receptor areas of each pressure sensor when no compressive force is applied to the sensor assembly.

19. The advanced compression garment of claim 18, wherein adjacent faces of the first substrate and the second substrate are joined to produce a sealed, water-resistant sensor assembly.

20. The advanced compression garment of claim 18, wherein the conductive ink is conductive silver ink and the substrates are a coextruded thermoplastic film.

21. The advanced compression garment of claim 18, wherein the connector includes:
- a conductive pad adapted to transfer electrical energy to the sensors via at least one of the flexible electrical conduits; and
- a plurality of additional conductive pads corresponding in number to the number of the sensors in the sensor assembly, the additional conductive pads adapted to transfer to the transmitter/transceiver data signals received from the sensors via the flexible electrical conduits.

22. The advanced compression garment of claim 21, wherein the connecting face comprises electrically conductive spring-loaded pins that are located and arranged to electrically connect with the conductive pads of the connector.

23. The advanced compression garment of claim 18, wherein the sensor assembly is applied directly to a garment layer.

24. A method of applying controllable and monitorable compression to a mammalian limb, head or torso, comprising:
(a) providing an advanced compression garment for donning over a portion of skin of the limb, the head or the torso of a wearer, the advanced compression garment comprising:
an inner layer encircling the skin and positioned to be in contact with the skin of the wearer,
a sensor assembly including a series of spaced apart pressure sensors in close proximity to the skin for sensing magnitude of compression of the advanced compression garment against the skin; the series of spaced apart pressure sensors distributed along a length of the inner layer;
an outer compressive layer in the form of a plurality of adjacent straps, the number of straps corresponding to the number of sensors, each strap attached at one end to the inner layer and adapted for at least partial wrapping under tension around the skin; and
a connector, distinct from the inner layer and attached to the inner layer, communicating with the sensor assembly; the connector holding a transmitter or a transceiver; the transmitter or transceiver comprising a housing including a first display on a first side and an opposed connecting face held by and in contact with the inner layer; the connecting face including magnetic tabs for attraction with the inner layer, wherein the transmitter or transceiver is releasably connected to the connector and the inner layer, adapted to communicate with the sensor assembly and communicate wirelessly with a monitor or monitor-controller remote from the inner layer;
the first display displaying first indications of pressure applied to the skin by the advanced compression garment; and
a second display of second indications of pressure applied to the skin displayed by the monitor or monitor-controller; the monitor's or monitor-controller's second display distinct from the first display;
(b) placing the advanced compression garment on the skin;
(c) tightening the straps to apply pressure to the skin, while simultaneously monitoring the level of applied pressure using the first display; and
(d) using the monitor or the monitor-controller including hardware and specialized software to analyze and display sensor data on the second display.

25. An advanced compression garment for a limb, a head or a torso of a wearer; the advanced compression garment comprising:
an inner layer in contact with skin of the wearer; the inner layer encircling a portion of the skin of the limb, the head or the torso;
a plurality of sensors proximate the skin sensing magnitude of compression of the advanced compression garment against the skin; the plurality of sensors connected with the advanced compression garment;
a connector, distinct from the inner layer, attached to the inner layer and communicating with one or more of the plurality of sensors; the connector adapted to hold either a transmitter or a transceiver; the transmitter or transceiver comprising a housing including a first display on a first side and an opposed connecting face held by and in contact with the inner layer; the connecting face including magnetic tabs for attraction with the inner layer, wherein the transmitter or transceiver is releasably connected to the connector and the inner layer, adapted to communicate with the plurality of sensors and communicate wirelessly with a monitor or monitor-controller remote from the inner layer;
the first display displaying first indications of pressure applied by the advanced compression garment, wherein the first indications portray distinct zones representing pressures sensed by each of the plurality of sensors for each distinct zone; and
an outer compressive layer adapted to contact the inner layer; the outer compressive layer controlling pressures applied to the inner layer.

26. The advanced compression garment of claim 25, wherein the transmitter or the transceiver generates an alert when pressure applied to the skin is different than preselected parameters.

27. The advanced compression garment of claim 26 comprising a second display of second indications of pressure applied to the skin displayed by the monitor or monitor-controller, wherein the monitor's or monitor-controller's second display is distinct from the first display.

28. The advanced compression garment of claim 27, wherein the plurality of sensors comprise force-sensing resistors, piezoelectric sensors, strain gauge sensors, near infrared spectroscopy sensors or any combination thereof.

29. The advanced compression garment of claim 28, wherein the plurality of sensors comprises force-sensing resistors printed on a substrate or a layer of the advanced compression garment.

30. The advanced compression garment of claim 27, wherein the transmitter or the transceiver communicates with the plurality of sensors via one or more conductive pads or conductive inks associated with the inner layer.

31. The advanced compression garment of claim 27, wherein the monitor-controller controls pressure applied to the skin.

32. The advanced compression garment of claim 31 further comprising a temperature sensor sensing temperature of the skin.

* * * * *

UNITED STATES PATENT AND TRADEMARK OFFICE
CERTIFICATE OF CORRECTION

PATENT NO. : 10,973,413 B2
APPLICATION NO. : 15/289071
DATED : April 13, 2021
INVENTOR(S) : Scott Rapp and Gary Rapp It is certified that error appears in the above-identified patent and that said Letters Patent is hereby corrected as shown below:

In the Claims

The below identified claims should read as follows:

3. The advanced compression garment of claim 2, wherein the at least one sensor is a plurality of sensors, wherein: the first indications are divided into a number of zones, each zone corresponding to a sensor of the plurality of sensors of the advanced compression garment.

4. The advanced compression garment of claim 2, wherein the at least one sensor is a plurality of sensors, wherein: second indications include a depiction of a human limb divided into a number of zones, each zone corresponding to a sensor of the plurality of sensors of the advanced compression garment; and wherein the monitor or the monitor-controller is adapted to apply any of several colors to each zone depending on a pressure condition indicated by the sensor associated with the given zone.

5. The advanced compression garment of claim 4, wherein the monitor or the monitor-controller includes control functionality by which settings and functions of the advanced compression garment may be manipulated.

Signed and Sealed this
First Day of October, 2024

Katherine Kelly Vidal
*Director of the United States Patent and Trademark Office*